United States Patent
Lo et al.

(10) Patent No.: US 9,218,449 B2
(45) Date of Patent: Dec. 22, 2015

(54) METHODS FOR ANALYZING MASSIVELY PARALLEL SEQUENCING DATA FOR NONINVASIVE PRENATAL DIAGNOSIS

(71) Applicant: The Chinese University of Hong Kong, Shatin, New Territories (HK)

(72) Inventors: Yuk Ming Dennis Lo, Kowloon (HK); Wai Kwun Rossa Chiu, Shatin (HK); Kwan Chee Chan, Kowloon (HK); Wenli Zheng, Shatin (HK); Hao Sun, Shatin (HK); Zhang Chen, Philadelphia, PA (US)

(73) Assignee: The Chinese University of Hong Kong, Shatin (CN)

( * ) Notice: Subject to any disclaimer, the term of this patent is extended or adjusted under 35 U.S.C. 154(b) by 0 days.

(21) Appl. No.: 13/802,268

(22) Filed: Mar. 13, 2013

(65) Prior Publication Data

US 2013/0245961 A1 Sep. 19, 2013

Related U.S. Application Data

(60) Provisional application No. 61/610,422, filed on Mar. 13, 2012.

(51) Int. Cl.
| | |
|---|---|
| *G06F 19/22* | (2011.01) |
| *G11C 17/00* | (2006.01) |
| *G06F 19/16* | (2011.01) |
| *G06F 19/18* | (2011.01) |

(52) U.S. Cl.
CPC ............... *G06F 19/16* (2013.01); *G06F 19/18* (2013.01); *G06F 19/22* (2013.01)

(58) Field of Classification Search
None
See application file for complete search history.

(56) References Cited

U.S. PATENT DOCUMENTS

| | | | |
|---|---|---|---|
| 7,371,525 B2 | 5/2008 | Tsui et al. |
| 7,718,367 B2 | 5/2010 | Lo et al. |
| 7,901,884 B2 | 3/2011 | Lo et al. |
| 8,288,100 B2 | 10/2012 | Lo et al. |
| 8,431,343 B2 | 4/2013 | Lo et al. |
| 8,442,774 B2 | 5/2013 | Lo et al. |
| 8,467,976 B2 | 6/2013 | Lo et al. |
| 2010/0138165 A1 | 6/2010 | Fan et al. |
| 2011/0039724 A1 | 2/2011 | Lo et al. |
| 2011/0276277 A1 | 11/2011 | Lo et al. |
| 2013/0237531 A1 | 9/2013 | Wu et al. |

FOREIGN PATENT DOCUMENTS

| | | |
|---|---|---|
| WO | 2004/029747 A2 | 4/2004 |
| WO | 2007/132167 A2 | 11/2007 |
| WO | 2011/054936 A1 | 5/2011 |
| WO | 2012/051346 A1 | 4/2012 |

OTHER PUBLICATIONS

Benjamini et al., "Summarizing and Correcting the GC Content Bias in High-Throughput Sequencing," Nucleic Acids Research, 40(10): 1-14 (2012).
Chen et al., "Noninvasive Prenatal Diagnosis of Fetal Trisomy 18 and Trisomy 13 by Maternal Plasma DNA Sequencing," PLoS ONE 6(7): e21791 (2011).
Fan et al., "Sensitivity of Noninvasive Prenatal Detection of Fetal Aneuploidy from Maternal Plasma Using Shotgun Sequencing is Limited Only by Counting Statistics," PLoS One (5): e10439 (2010).
Lau et al., "Noninvasive Prenatal Diagnosis of Common Fetal Chromosomal Aneuploidies by Maternal Plasma DNA Sequencing," Journal of Maternal-Fetal and Neonatal Medicine, 25(8): 1370-1374 (2012).
Boeva et al., "Control-Free Calling of Copy Number Alternations in Deep-Sequencing Data using GC-Content Normalization," Bioinformatics, 27(2): 268-269 (2011).
Chiu et al., "Maternal Plasma DNA Analysis with Massively Parallel Sequencing by Ligation for Noninvasive Prenatal Diagnosis of Trisomy 21," Clinical Chemistry 56(3): 459-463 (2010).
Gao et al., "GC-Profile: A Web-Based Tool for Visualizing and Analyzing the Variation of GC Content in Genomic Sequences," Nucleic Acids Research, 34: W686-W691 (2006).
Risso et al., "GC-Content Normalization for RNA-Seq Data," BMC Bioinformatics, 12: 480 (2011).
Supplementary European Search Report mailed Jul. 30, 2015 in EP Patent Application No. 13760635, 11 pages.

*Primary Examiner* — John S Brusca

(74) *Attorney, Agent, or Firm* — Kilpatrick Townsend & Stockton LLP

(57) ABSTRACT

This invention provides several ways of managing GC bias that occurs during seequencing and analysis of genomic DNA. Maternal plasma can be used as a source of fetal DNA for analysis. DNA segments or tags obtained from the plasma can be aligned with a chromosomal region of interest and with an artificial reference chromosome assembled from regions of the genome having matching GC content. This technology can be used, for example, to detect and evaluate aneuploidy and other chromosomal abnormalities.

30 Claims, 23 Drawing Sheets

| Bin size (bp) | CVs (%) | |
|---|---|---|
| | Chr13 | Chr18 |
| 1M | 0.302 | 0.341 |
| 500K | 0.298 | 0.338 |
| 100K | 0.302 | 0.333 |
| 50K | 0.310 | 0.334 |

|  | CVs (%) | |
| --- | --- | --- |
|  | chr21 | chr18 |
| GC correction | 0.31% | 0.33% |
| Modified genomic representation | 0.47% | 0.39% |
| Combined | 0.37% | 0.38% |

Chromosome 13

Long arm of Chr.13: 98.1Mb

Region1    16-52.9Mb
Region2    52.9-90.7Mb
Region3    90.7-114.1Mb

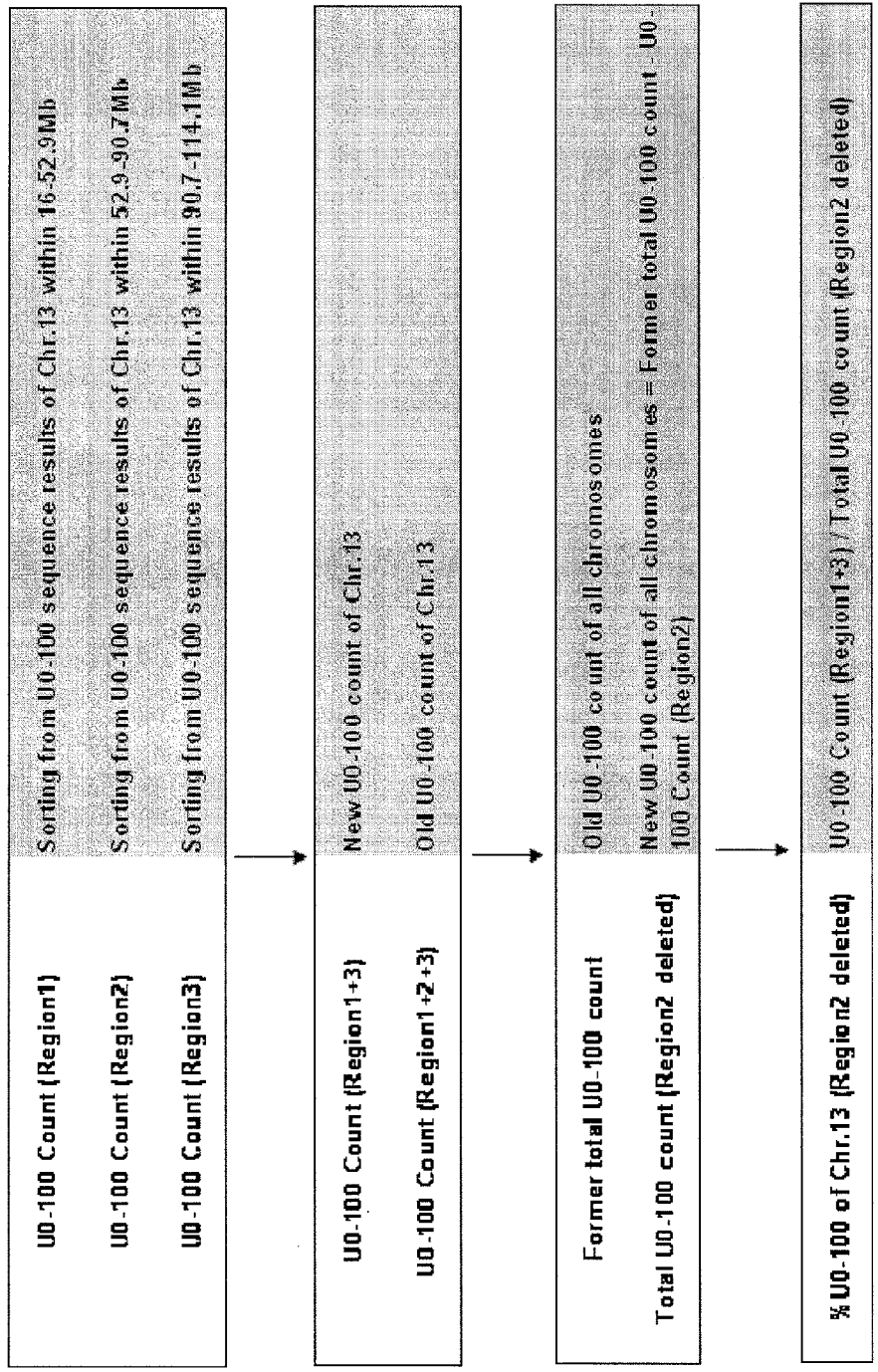

Compare z-score

Old analysis

New analysis

METHODS FOR ANALYZING MASSIVELY PARALLEL SEQUENCING DATA FOR NONINVASIVE PRENATAL DIAGNOSIS

CROSS-REFERENCES TO RELATED APPLICATIONS

This application claims the priority benefit of U.S. application 61/610,422, filed Mar. 13, 2012.

The priority application is hereby incorporated herein by reference in its entirety for all purposes. U.S. patent applications 60/951,438, filed Jul. 23, 2007; and Ser. No. 12/178, 116, filed Jul. 23, 2008 (pending) are also hereby incorporated herein by reference in their entirety for all purposes.

BACKGROUND

Massively parallel sequencing of circulating fetal nucleic acids has been used for noninvasive prenatal diagnosis. It is known that quantitative biases in the representation of sequenced reads may be related to a number of factors, including the GC content of the sequenced template DNA.

SUMMARY

This disclosure describes several methods to reduce (i.e. minimize) the degree of quantitative biases observed. As a result of such embodiments, the sequencing data can more accurately reflect the true relative distributions between template DNA molecules in the original sample and hence enable more accurate clinical diagnosis.

Embodiments of the invention are directed to systems and computer readable media associated with methods described below.

BRIEF DESCRIPTION OF THE DRAWINGS

FIGS. 10A, 10B, and 10C. DNA sequence analysis of human chromosome 13. (A) Both Regions 1 and 3 have a GC content of 39%; while Region 2 has a GC content that drops to 33%. (B) is a schematic illustration of the data analysis steps. (C) shows the z-score of a T13 case.

DEFINITIONS

Figure 1:
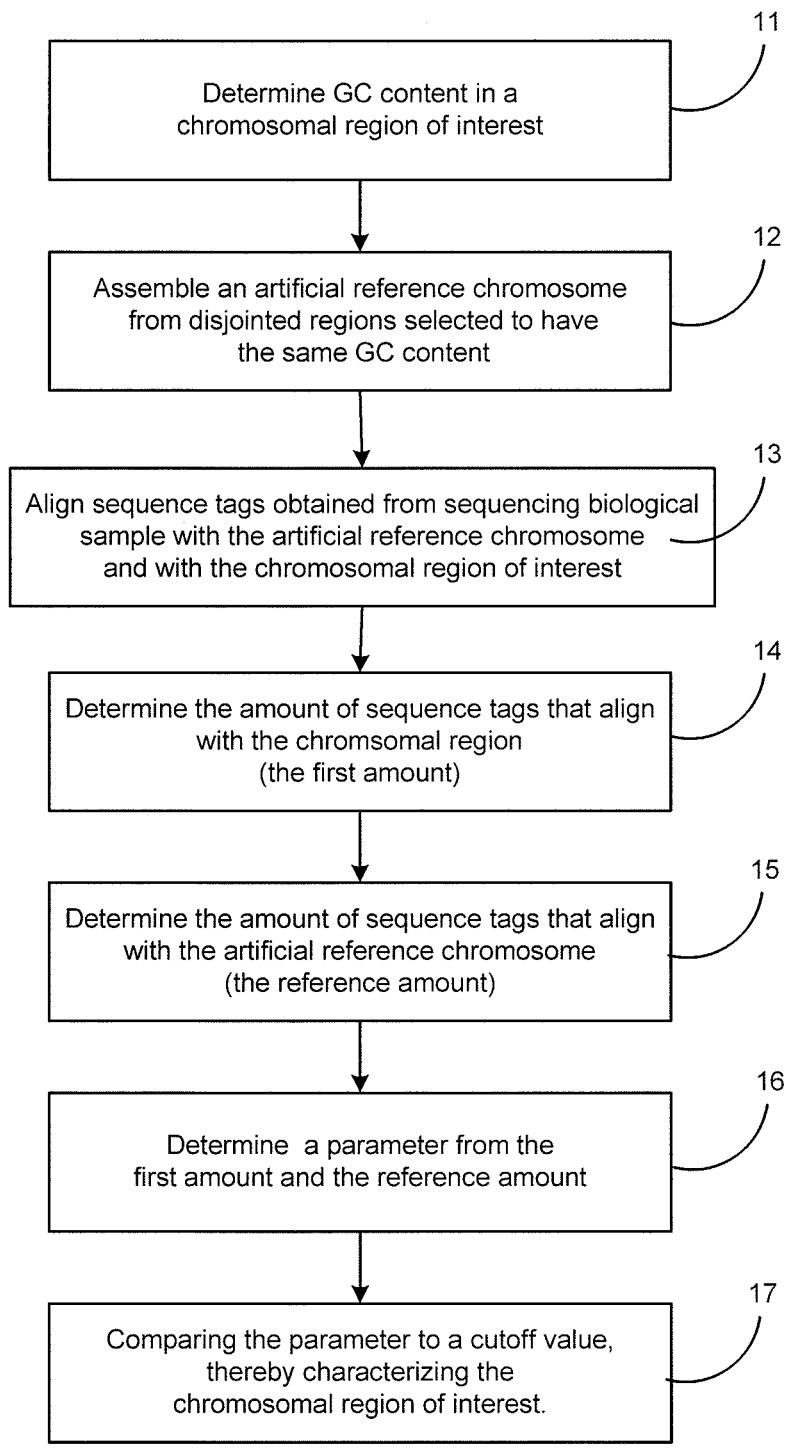
FIG. 1 is a flow chart showing a method of reducing GC bias by aligning sequences obtained from maternal plasma with an artificial chromosome.

The term "biological sample" as used herein refers to any sample that is taken from a subject (e.g., a human, such as a pregnant woman) and contains one or more nucleic acid molecule(s) of interest.

The term "nucleic acid" or "polynucleotide" refers to a deoxyribonucleic acid (DNA) or ribonucleic acid (RNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, mRNA, small noncoding RNA, micro RNA (miRNA), Piwi-interacting RNA, and short hairpin RNA (shRNA) encoded by a gene or locus.

The term "gene" means the segment of DNA involved in producing a polypeptide chain. It may include regions preceding and following the coding region (leader and trailer) as well as intervening sequences (introns) between individual coding segments (exons).

The term "reaction" as used herein refers to any process involving a chemical, enzymatic, or physical action that is indicative of the presence or absence of a particular polynucleotide sequence of interest. An example of a "reaction" is an amplification reaction such as a polymerase chain reaction (PCR). Another example of a "reaction" is a sequencing reaction, either by synthesis or by ligation. An "informative reaction" is one that indicates the presence of one or more particular polynucleotide sequence of interest, and in one case where only one sequence of interest is present. The term "well" as used herein refers to a reaction at a predetermined location within a confined structure, e.g., a well-shaped vial, cell, or chamber in a PCR array.

The term "clinically relevant nucleic acid sequence" as used herein can refer to a polynucleotide sequence corresponding to a segment of a larger genomic sequence whose potential imbalance is being tested or to the larger genomic sequence itself. One example is the sequence of chromosome 21. Other examples include chromosome 18, 13, X and Y. Yet other examples include mutated genetic sequences or genetic polymorphisms or copy number variations that a fetus may inherit from one or both of its parents. Yet other examples include sequences which are mutated, deleted, or amplified in a malignant tumor, e.g. sequences in which loss of heterozygosity or gene duplication occur. In some embodiments, multiple clinically relevant nucleic acid sequences, or equivalently multiple makers of the clinically relevant nucleic acid sequence, can be used to provide data for detecting the imbalance. For instance, data from five non-consecutive sequences on chromosome 21 can be used in an additive fashion for the determination of possible chromosomal 21 imbalance, effectively reducing the need of sample volume to 1/5.

The term "background nucleic acid sequence" as used herein refers to a nucleic acid sequence whose normal ratio to the clinically relevant nucleic acid sequence is known, for instance a 1-to-1 ratio. As one example, the background nucleic acid sequence and the clinically relevant nucleic acid sequence are two alleles from the same chromosome that are distinct due to heterozygosity. In another example, the background nucleic acid sequence is one allele that is heterozygous to another allele that is the clinically relevant nucleic acid sequence. Moreover, some of each of the background nucleic acid sequence and the clinically relevant nucleic acid sequence may come from different individuals.

The term "reference nucleic acid sequence" as used herein refers to a nucleic acid sequence whose average concentration per reaction is known or equivalently has been measured.

The term "overrepresented nucleic acid sequence" as used herein refers to the nucleic acid sequence among two sequences of interest (e.g., a clinically relevant sequence and a background sequence) that is in more abundance than the other sequence in a biological sample.

The term "based on" as used herein means "based at least in part on" and refers to one value (or result) being used in the determination of another value, such as occurs in the relationship of an input of a method and the output of that method. The term "derive" as used herein also refers to the relationship of an input of a method and the output of that method, such as occurs when the derivation is the calculation of a formula.

The term "quantitative data" as used herein means data that are obtained from one or more reactions and that provide one or more numerical values. For example, the number of wells that show a fluorescent marker for a particular sequence would be quantitative data.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

The term "cutoff value" as used herein means a numerical value whose value is used to arbitrate between two or more states (e.g. diseased and non-diseased) of classification for a biological sample. For example, if a parameter is greater than the cutoff value, a first classification of the quantitative data is made (e.g. diseased state); or if the parameter is less than the cutoff value, a different classification of the quantitative data is made (e.g. non-diseased state).

The term "imbalance" as used herein means any significant deviation as defined by at least one cutoff value in a quantity of the clinically relevant nucleic acid sequence from a reference quantity. For example, the reference quantity could be a ratio of 3/5, and thus an imbalance would occur if the measured ratio is 1:1.

The term "chromosomal aneuploidy" as used herein means a variation in the quantitative amount of a chromosome from that of a diploid genome. The variation may be a gain or a loss. It may involve the whole of one chromosome or a region of a chromosome.

The term "random sequencing" as used herein refers to sequencing whereby the nucleic acid fragments sequenced have not been specifically identified or targeted before the sequencing procedure. Sequence-specific primers to target specific gene loci are not required. The pools of nucleic acids sequenced vary from sample to sample and even from analysis to analysis for the same sample. The identities of the sequenced nucleic acids are only revealed from the sequencing output generated. In some embodiments of the present invention, the random sequencing may be preceded by procedures to enrich a biological sample with particular populations of nucleic acid molecules sharing certain common features. In one embodiment, each of the fragments in the biological sample have an equal probability of being sequenced.

The term "fraction of the human genome" or "portion of the human genome" as used herein refers to less than 100% of the nucleotide sequences in the human genome which comprises of some 3 billion basepairs of nucleotides. In the context of sequencing, it refers to less than 1-fold coverage of the nucleotide sequences in the human genome. The term may be expressed as a percentage or absolute number of nucleotides/basepairs. As an example of use, the term may be used to refer to the actual amount of sequencing performed. Embodiments may determine the required minimal value for the sequenced fraction of the human genome to obtain an accurate diagnosis. As another example of use, the term may refer to the amount of sequenced data used for deriving a parameter or amount for disease classification.

The term "sequenced tag" as used herein refers to string of nucleotides sequenced from any part or all of a nucleic acid molecule. For example, a sequenced tag may be a short string of nucleotides sequenced from a nucleic acid fragment, a short string of nucleotides at both ends of a nucleic acid fragment, or the sequencing of the entire nucleic acid fragment that exists in the biological sample. A nucleic acid fragment is any part of a larger nucleic acid molecule. A fragment (e.g. a gene) may exist separately (i.e. not connected) to the other parts of the larger nucleic acid molecule.

DETAILED DESCRIPTION

I. Improving Alignment

To improve detection accuracy, one way is to improve the alignment in the bioinformatics analysis procedure, so that more aligned reads could be obtained. To achieve this goal, several possible solutions could be considered.

Allowing Mismatches in the Index Sequences

Due to the sequencing error and other potential problems in the sample preparation process, it is possible that the index sequences that have been sequenced might not be exactly the same as those originally designed. Consequently, those reads with the unmatched index sequence could not be sorted back to its corresponding sample.

A total of 12 index sequences were provided by Illumina for multiplex sequencing. These index sequences were used in plasma DNA sequencing with 2-plex sequencing strategy in this study. Two samples were sequenced in the same sequencing lane and each of them was assigned one of the index sequences. During the sequencing process, the index sequences would also be sequenced. After sequencing, the reads from the two samples in the same lane were mixed together and would be sorted back to the corresponding samples according the index sequences.

The mismatch of the index sequence was defined as the different nucleotides between the sequenced one and originally designed one. The maximum mismatches in the index sequence was defined as the maximum different nucleotides allowable with which one index sequence was still different from all the other ones. To find the maximum mismatches allowable in one index sequence, all the possible sequences with 0, 1, 2 ... n mismatches were enumerated and compared with all the other index sequences, until one of the possible sequences was the same as one of the other index.

One possible way to increase the uniquely aligned reads was to allow mismatches in the index sequences when sorting reads back to the corresponding samples. The maximum mismatches allowable in one index sequence with which it could still be distinguishable (Table 4.1). For all the index sequences, at least 2 mismatches could be allowed. A more stringent criterion which allowed only 1 mismatch was used in the following analysis.

TABLE 4.1

The maximum mismatches allowable in the index sequences

| Index number | Index sequence | Maximum mismatches allowable |
|---|---|---|
| 1 | ATCACG | 3 |
| 2 | CGATGT | 3 |
| 3 | TTAGGC | 3 |
| 4 | TGACCA | 3 |
| 5 | ACAGTG | 3 |
| 6 | GCCAAT | 2 |
| 7 | CAGATC | 2 |
| 8 | ACTTGA | 3 |
| 9 | GATCAG | 3 |
| 10 | TAGCTT | 2 |
| 11 | GGCTAC | 2 |
| 12 | CTTGTA | 3 |

Figure 2A:
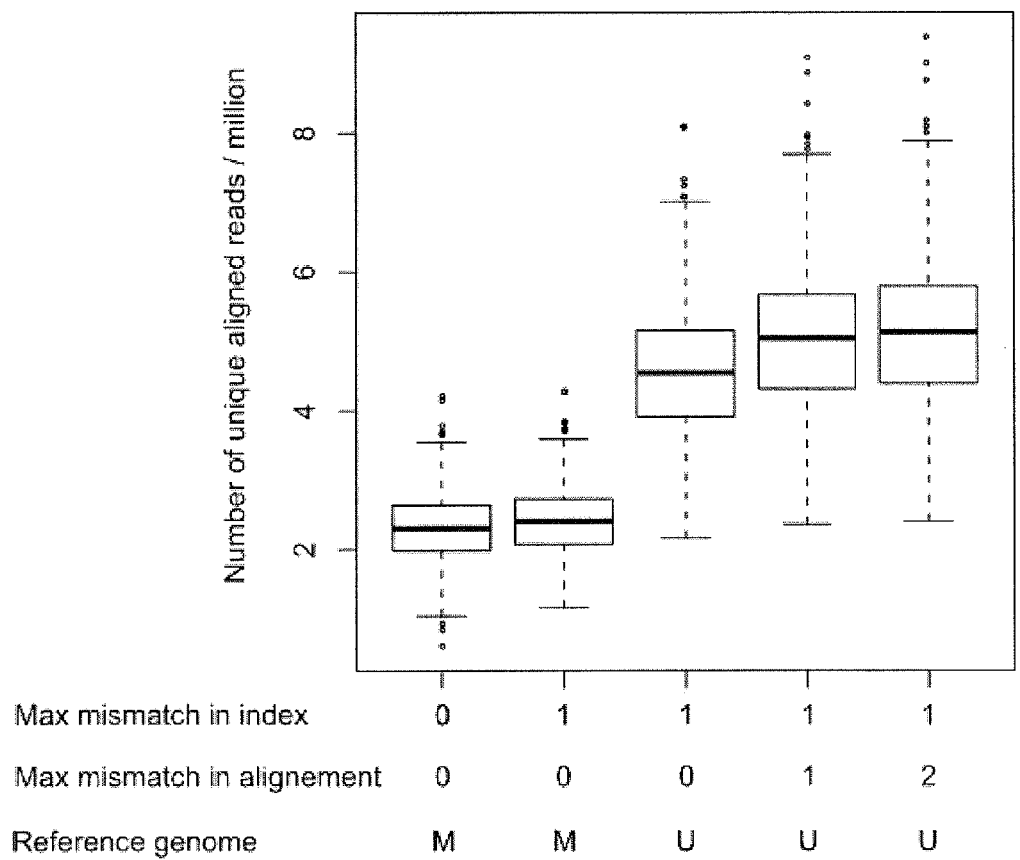
FIG. 2A. The number of uniquely aligned reads with different analysis criteria The boxplot of uniquely aligned reads for all the sequenced samples with different analysis criteria. M, repeat masked human reference genome. U, non-repeat masked human reference genome.

The maximum mismatches in the index sequence was defined as the maximum different nucleotides allowable in the sequence with which one index sequence was still different from all the other ones. Without mismatch allowable in the index sequences, an average of 2.3 million (SD 517,888) uniquely aligned reads per sample was obtained (FIG. 2A and Table 4.4). Three samples had relatively low uniquely aligned reads (less than one million). The average sequencing coverage was 2.7% (SD 0.61%) per sample.

The sequencing data were then re-analyzed by allowing one mismatch in the index sequences. The average number of uniquely aligned reads for each sample was 2.4 million (SD 508,842). The average percentage of increase was 6.0% (SD 21.7%) compared to the analysis when no mismatch was allowed in the index sequences. After allowing one mismatch in the index sequences, the read number of 12 samples increased more than 50%. Among these samples, three samples with less than 1 million aligned reads in the previous analysis had more than 2 million reads after allowing one mismatch.

Figure 2B:
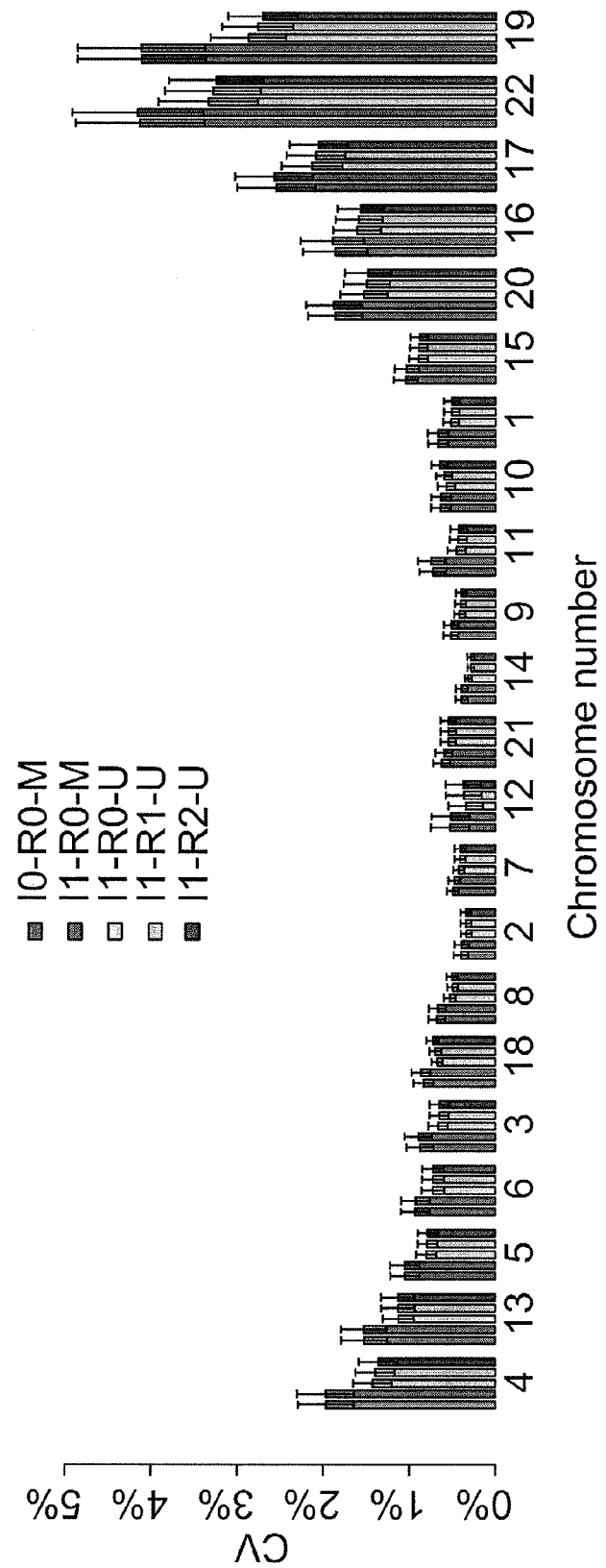
FIG. 2B The precision of quantifying autosomes with different alignment parameters. The chromosomes were ordered from left to right in increasing GC contents. 95% confidence interval was shown in error bars. I, number of mismatches allowable in the index sequence. R, number of mismatches allowable in the read alignment. M, repeat masked human reference genome. U, non-repeat masked human reference genome.

Next, the CVs for quantifying the autosomes were calculated based on the analysis with 1 mismatch allowable in the index (FIG. 2B and Table 4.5). For chr13, the CVs slightly increased from 15.2% to 15.3%. For chr18, the CVs also increased from 8.31% to 8.60%. Although the CVs of quantifying autosomes was slightly worse, considering the increase in read numbers, especially for those samples with possible errors in the sequenced index sequence, 1 mismatch allowable in the index sequence was used in the following analysis.

Increasing Read Numbers by Using the Non-masked Reference Genome for Alignment

Second, a non-masked human reference genome could be used instead of a repeat masked one as the alignment reference. In the repeat masked reference genome, the repetitive sequences were masked and thus these regions were excluded for alignment. In order to exclude the reads from the repeat regions, which might have multiple alignments, the repeat masked genome was adapted as an alignment reference in the T21 analysis pipeline.

In order to study whether the reads from repetitive regions of the human reference genome could be uniquely aligned, a simulation was performed on the non-repeat masked human reference genome (Hg18 NCBI.36). The non-repeat masked human reference genome was divided into N-bp simulated reads with 1-bp shift. N was 36, 50 or 75 which was the most common read length generated from the Illumina sequencing platform. Those simulated reads were then aligned back to the non-repeat masked human reference genome with no mismatch allowable by SOAP2. If a simulated read could be uniquely aligned back to the reference genome, it would be retained and the start position of the simulation read would be defined as mappable. The mappability of a particular region was then defined as the percentage of mappable nucleotides over the total nucleotides in this region. The 'N' nucleotides in the non-repeat masked human reference genome were excluded in the analysis.

Before testing the alignment on the non-repeat masked reference genome, it was determined whether the reads from the repeat regions could be uniquely aligned by the simulation study. As showed in Table 4.2, around 48.8% of the human reference genome was repeat sequences. Those sequences were masked in the repeat masked human reference genome. If the repeat masked genome was used as alignment reference, reads from these regions could not be aligned back and thus would be excluded for further analysis. However, by computer simulation with the 36 by simulated reads, 77.4% of the repeat regions could actually be uniquely aligned. The unique alignment rate of the repeat regions increased to 86.7% and 93.4% with the 50 by and 75 by simulated reads, respectively (Table 4.3). For the non-repeat regions, around 96.3%, 96.8% and 97.4% could be uniquely aligned with 36 bp, 50 by and 75 by simulated reads, respectively. This indicated that increasing the sequenced read length would help increase the unique alignment rate, especially for the repeat regions.

Next, the raw sequencing reads from all the samples were re-aligned to the non-repeat masked human reference genome. After sorting back the reads into the corresponding samples with one mismatch allowable, average 4.6 million (SD 964,095) of uniquely aligned reads per sample were obtained (FIG. 2A and Table 4.4). The uniquely aligned reads increase by 89% compared to the alignment with the repeat masked genome. As shown in FIG. 2B and Table 4.5, the precision of measuring the autosomes was improved. Particularly, for chr13, the CVs decreased from 1.53% to 1.12%. Similarly, the CVs for chr18 also decreased from 0.86% to 0.67%. This indicated that the precision of measuring chr13 and chr18 had been improved after using the non-repeat masked human genome as the alignment reference. Therefore, this alignment criterion would be adapted in the following analysis.

TABLE 4.2

The proportion of the repeat and non-repeat sequences in the human genome.

| Chromosome | Total informative region (million bp) | Non-repeat sequences (million bp) | | Repeat sequences (million bp) | |
|---|---|---|---|---|---|
| chr1 | 225.0 | 115.3 | 51.2% | 109.7 | 48.8% |
| chr2 | 237.7 | 127.5 | 53.6% | 110.2 | 46.4% |
| chr3 | 194.7 | 101.0 | 51.8% | 93.8 | 48.2% |
| chr4 | 187.3 | 95.6 | 51.0% | 91.7 | 49.0% |
| chr5 | 177.7 | 92.2 | 51.9% | 85.5 | 48.1% |
| chr6 | 167.3 | 88.2 | 52.7% | 79.1 | 47.3% |
| chr7 | 155.0 | 80.3 | 51.8% | 74.7 | 48.2% |
| chr8 | 142.6 | 73.7 | 51.6% | 69.0 | 48.4% |
| chr9 | 120.1 | 61.9 | 51.5% | 58.2 | 48.5% |
| chr10 | 131.6 | 70.0 | 53.2% | 61.6 | 46.8% |
| chr11 | 131.1 | 66.8 | 50.9% | 64.3 | 49.1% |
| chr12 | 130.3 | 65.5 | 50.3% | 64.8 | 49.7% |
| chr13 | 95.6 | 51.7 | 54.1% | 43.9 | 45.9% |
| chr14 | 88.3 | 45.8 | 51.8% | 42.5 | 48.2% |
| chr15 | 81.3 | 42.9 | 52.8% | 38.4 | 47.2% |
| chr16 | 78.9 | 40.2 | 51.0% | 38.7 | 49.0% |
| chr17 | 77.8 | 40.8 | 52.5% | 37.0 | 47.5% |
| chr18 | 74.7 | 41.0 | 55.0% | 33.6 | 45.0% |
| chr19 | 55.8 | 24.1 | 43.1% | 31.7 | 56.9% |
| chr20 | 59.5 | 30.5 | 51.2% | 29.0 | 48.8% |
| chr21 | 34.2 | 18.4 | 53.9% | 15.8 | 46.1% |
| chr22 | 34.9 | 18.1 | 52.0% | 16.7 | 48.0% |
| chrX | 151.1 | 61.6 | 40.8% | 89.4 | 59.2% |
| chrY | 25.7 | 9.7 | 37.9% | 15.9 | 62.1% |
| chrM | 0.0 | 0.0 | 97.7% | 0.0 | 2.3% |
| Total | 2858.0 | 1462.7 | 51.2% | 1395.3 | 48.8% |

'N's in the genome sequences were excluded for analysis.

TABLE 4.3

The percentage of mappable sequences in the repeat and non-repeat regions of the human genome

| Chromosome | Mappable fraction of non-repeat region | | | Mappable fraction of repeat region | | |
|---|---|---|---|---|---|---|
| | 36bp | 50bp | 75bp | 36bp | 50bp | 75bp |
| chr1 | 95.9% | 96.4% | 97.0% | 77.1% | 86.6% | 93.6% |
| chr2 | 96.9% | 97.4% | 97.9% | 79.2% | 87.9% | 94.3% |
| chr3 | 99.1% | 99.4% | 99.7% | 80.3% | 89.1% | 95.4% |
| chr4 | 98.5% | 98.8% | 99.2% | 80.2% | 88.6% | 94.7% |
| chr5 | 97.5% | 97.9% | 98.2% | 78.9% | 87.5% | 93.8% |
| chr6 | 98.6% | 99.0% | 99.3% | 79.4% | 88.5% | 95.1% |
| chr7 | 95.4% | 96.3% | 97.1% | 76.1% | 85.9% | 93.1% |
| chr8 | 98.0% | 98.4% | 98.7% | 80.4% | 88.9% | 94.8% |
| chr9 | 90.5% | 91.2% | 92.0% | 71.8% | 80.6% | 87.3% |
| chr10 | 95.6% | 96.1% | 96.7% | 77.1% | 86.5% | 93.2% |
| chr11 | 97.8% | 98.4% | 98.9% | 79.0% | 88.1% | 94.7% |
| chr12 | 98.6% | 99.0% | 99.4% | 78.8% | 88.7% | 95.7% |
| chr13 | 98.5% | 98.9% | 99.3% | 82.0% | 90.1% | 95.8% |
| chr14 | 97.9% | 98.3% | 98.7% | 78.4% | 88.0% | 94.8% |
| chr15 | 93.0% | 93.9% | 94.7% | 75.4% | 85.1% | 92.2% |
| chr16 | 92.8% | 93.6% | 94.6% | 73.6% | 84.3% | 91.8% |
| chr17 | 94.6% | 95.6% | 96.6% | 71.9% | 84.5% | 93.9% |
| chr18 | 98.4% | 98.8% | 99.2% | 81.4% | 89.6% | 95.5% |
| chr19 | 95.4% | 96.8% | 97.9% | 70.6% | 85.1% | 95.3% |
| chr20 | 98.4% | 98.9% | 99.3% | 80.7% | 89.9% | 96.4% |
| chr21 | 97.0% | 97.8% | 98.6% | 80.1% | 89.3% | 95.7% |
| chr22 | 92.2% | 93.4% | 94.6% | 72.1% | 83.8% | 92.6% |
| chrX | 93.4% | 94.0% | 94.7% | 75.3% | 83.9% | 90.2% |
| chrY | 47.1% | 49.9% | 52.8% | 43.6% | 50.3% | 56.3% |
| chrM | 67.4% | 76.4% | 85.1% | 65.7% | 74.3% | 85.8% |
| Total | 96.3% | 96.8% | 97.4% | 77.4% | 86.7% | 93.4% |

Aligning Reads to the Non-repeat Masked Human Reference Genome

In the previous analysis, only the perfectly aligned reads were retained. Similarly, due to sequencing error and the presence of polymorphisms in the human genome, the sequenced reads might not be exactly the same as its corresponding reference genomic sequences. Allowing mismatch in the read alignment was thus a possible way to increase the aligned reads.

A non-repeat masked human reference genome (Hg18 NCBI.36) instead of the repeat masked one was tested as the alignment reference. Reads were aligned by SOAP2. A maximum of 0, 1 and 2 mismatches allowable in the read alignment were also tested.

The alignment was tested by allowing one, or two mismatches based on the non-repeat masked genome. Compared with the alignment with no mismatch allowable, the uniquely aligned reads increased by 9.06% and 10.95% with one and two mismatches, respectively (FIG. 2A and Table 4.4).

As shown in FIG. 2B and Table 4.5, the CVs for measuring chr13 were 1.12%, 1.13% and 1.13% with zero, one and two mismatches allowable, respectively. For chr18, the CVs were 0.67%, 0.69% and 0.73% with zero, one and two mismatches allowable, respectively. CVs for measuring chr13 and chr18 increased when more mismatches being allowable in the alignment. Thus, the precision of measuring chr13 and chr18 was worse when more mismatches were allowed. Therefore, no mismatch was allowed in the following analysis.

Results

TABLE 4.4

The number of uniquely aligned reads with different analysis criteria

| Index mismatches | Alignment mismatches | Reference genome | Uniquely aligned reads | | | |
|---|---|---|---|---|---|---|
| | | | Mean | SD | Min | Max |
| 0 | 0 | Masked | 2,318,545 | 517,888 | 599,711 | 4,213,771 |
| 1 | 0 | Masked | 2,417,346 | 508,842 | 1,151,610 | 4,277,572 |
| 1 | 0 | Unmasked | 4,568,735 | 964,095 | 2,163,261 | 8,098,248 |
| 1 | 1 | Unmasked | 5,034,327 | 1,063,357 | 2,359,269 | 9,082,907 |
| 1 | 2 | Unmasked | 5,137,919 | 1,085,926 | 2,400,177 | 9,379,106 |

Masked, repeat masked human reference genome. Unmasked, non-repeat masked human reference genome.

TABLE 4.5

CVs of quantifying autosomes with different alignment parameters

| | CVs (%) | | | | |
|---|---|---|---|---|---|
| Chromosome | I0-R0-M | I1-R0-M | I1-R0-U | I1-R1-U | I1-R2-U |
| chr4 | 1.96 | 1.97 | 1.42 | 1.39 | 1.36 |
| chr13 | 1.52 | 1.53 | 1.12 | 1.13 | 1.13 |
| chr5 | 1.05 | 1.05 | 0.8 | 0.79 | 0.78 |
| chr6 | 0.93 | 0.92 | 0.72 | 0.72 | 0.72 |
| chr3 | 0.87 | 0.89 | 0.66 | 0.65 | 0.65 |
| chr18 | 0.83 | 0.86 | 0.67 | 0.69 | 0.73 |
| chr8 | 0.68 | 0.67 | 0.53 | 0.5 | 0.5 |
| chr2 | 0.4 | 0.39 | 0.34 | 0.34 | 0.34 |
| chr7 | 0.5 | 0.48 | 0.43 | 0.41 | 0.41 |
| chr12 | 0.53 | 0.52 | 0.34 | 0.37 | 0.37 |
| chr21 | 0.62 | 0.6 | 0.55 | 0.54 | 0.55 |
| chr14 | 0.39 | 0.39 | 0.32 | 0.29 | 0.29 |
| chr9 | 0.52 | 0.52 | 0.42 | 0.41 | 0.4 |
| chr11 | 0.73 | 0.75 | 0.45 | 0.43 | 0.43 |
| chr10 | 0.64 | 0.63 | 0.57 | 0.6 | 0.65 |
| chr1 | 0.67 | 0.67 | 0.52 | 0.51 | 0.51 |
| chr15 | 1.04 | 1.03 | 0.89 | 0.89 | 0.88 |
| chr20 | 1.87 | 1.89 | 1.53 | 1.5 | 1.48 |
| chr16 | 1.87 | 1.9 | 1.61 | 1.59 | 1.57 |
| chr17 | 2.56 | 2.58 | 2.14 | 2.09 | 2.06 |
| chr22 | 4.15 | 4.17 | 3.35 | 3.3 | 3.26 |
| chr19 | 4.13 | 4.13 | 2.89 | 2.78 | 2.72 |

I number of mismatches allowable in the index sequence.
R number of mismatches allowable in the read alignment.
M repeat masked human reference genome.
U non-repeat masked human reference genome.
Chromosomes were ordered from top to bottom in increasing GC contents.

Trisomy 13 and 18

Figure 2C:
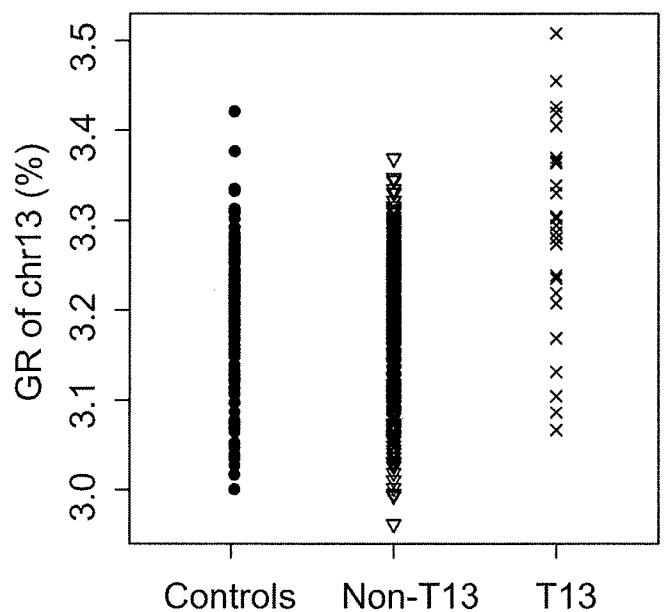
FIGS. 2C and 2D Trisomy 13 detection by the T21 bioinformatics analysis pipeline with improved alignment. (C) The genomic representation of chr13 for the trisomy 13, non-trisomy 13 and control samples (D) The z score of chr13 for the trisomy 13, non-trisomy 13 and control samples. Dashed line indicated the diagnostic cutoff with a z score value of 3. T13, trisomy 13. GR, genomic representation.
Figure 2D:
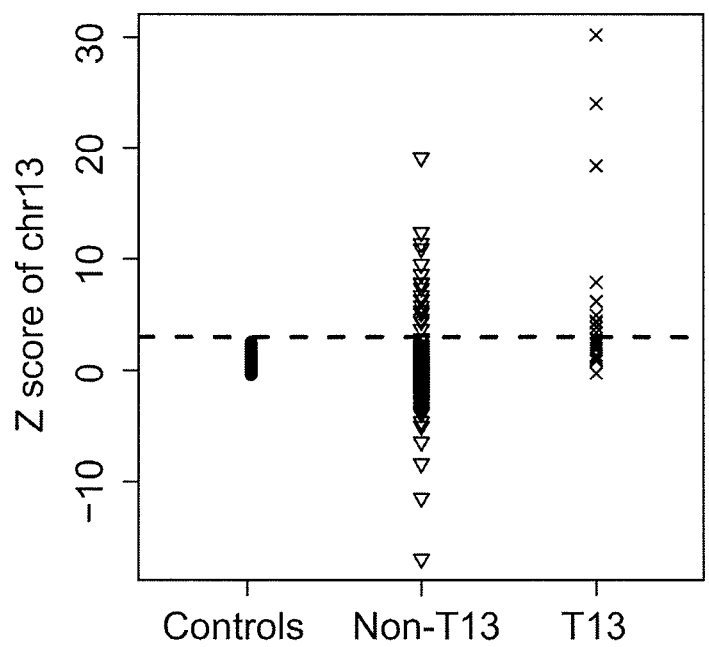
Figure 2E:
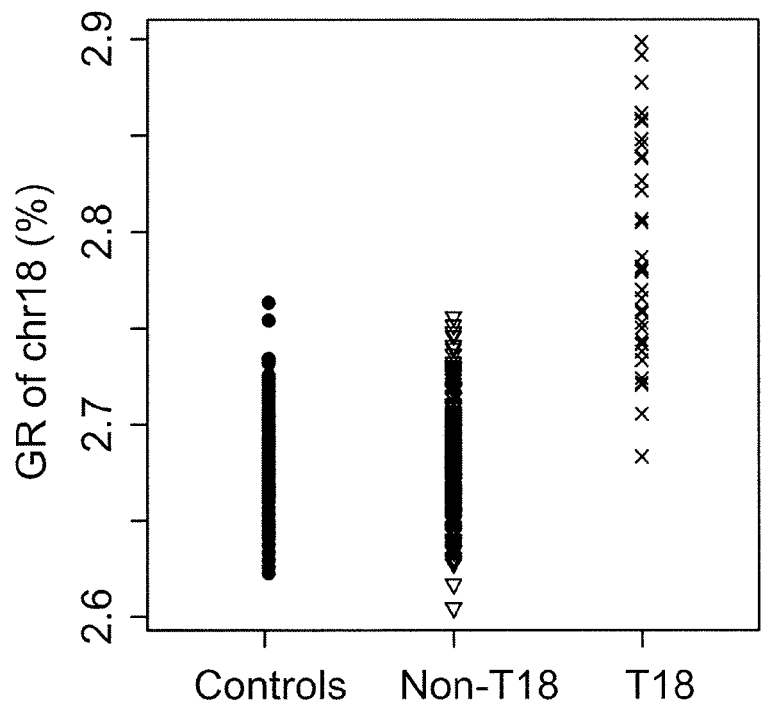
FIGS. 2E and 2F. Trisomy 18 detection by the T21 bioinformatics analysis pipeline with improved alignment. (E) The genomic representation of chr18 for the trisomy 18, non-trisomy 18 and control samples (F) The z score of chr18 for the trisomy 18, non-trisomy 18 and control samples. Dashed line indicated the diagnostic cutoff with a z score value of 3. T18, trisomy 18. GR, genomic representation.
Figure 2F:
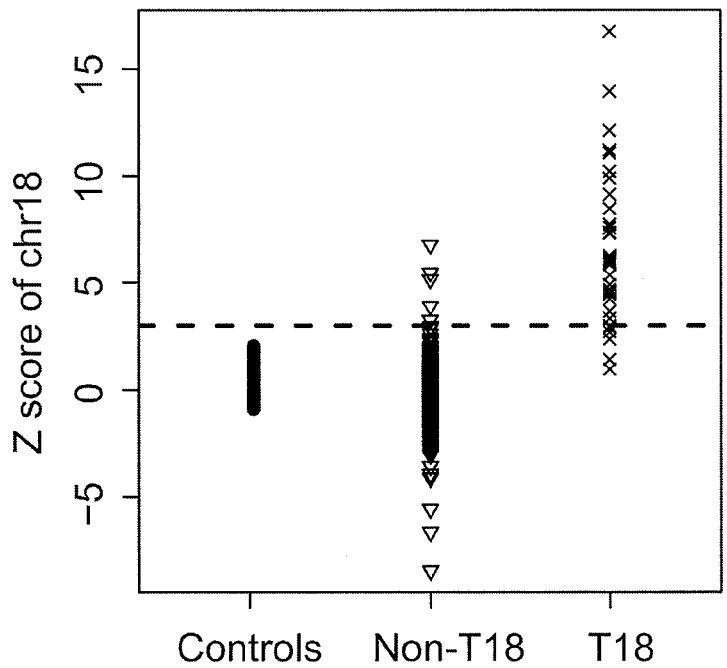

After the improvement of the alignment step in the T21 bioinformatics analysis pipeline, the performance of the trisomy 13 and 18 was tested by calculating the z score. For trisomy 13, 11 of 25 trisomy 13 cases and 247 of 264 non-trisomy 13 cases were correctly identified, corresponding to an improved sensitivity and specificity of 44.0% and 93.6%, respectively (FIG. 2C). For trisomy 18, 31 of 37 trisomy 18 cases and 247 of 252 non-trisomy 18 cases were correctly identified, corresponding to sensitivity and specificity of 83.8% and 98.0%, respectively (FIG. 2D). These results indicated that after improving the alignment step in the T21 bioinformatics analysis pipeline, the performance of trisomy 13 and 18 detection by NGS had been improved. However, compared to the trisomy 21 detection, the detection rate for trisomy 13 and 18 was still suboptimal.

To improve the alignment step, three aspects in the alignment step have been discussed, including using the non-repeat masked human genome instead of the repeat masked one as the alignment reference, allowing mismatches in the index sequences and read alignment.

After using the non-repeat masked genome as the alignment reference, the average aligned reads increased by 2.2 million which was 1.9 times than that by using the repeat masked reference genome. All these increased reads were from the repeat regions that had been masked in the repeat masked genome. The simulation analysis showed that 77.4% of the repeat regions, taking up 48.8% of the human genome, could be uniquely aligned with the 36 by simulated reads. This was probably due to the fact that a large proportion of the repeat sequences in the human genome share certain similarity but not exact the same. Although these repeat elements have multiple copies in the human genome, but each of them are not exactly the same, which unlike the simple repeats that have exactly the same repeat unit. Thus those reads from such repeat regions could be uniquely aligned back. Therefore it was better to use the non-repeat masked human genome than the repeat masked one as the alignment reference.

When the length of simulating read increased, the uniquely aligned proportion of the repeat region and non-repeat regions increased. Compared with simulation result with 36 by simulated reads, the percentage of uniquely aligned regions increased by 0.5% (50 bp), 1.1% (75 bp) for the non-repeat sequences and 9.3% (50 bp), 16.0% (75 bp) for the repeat sequences, respectively. This indicated that increasing the length of sequenced reads will improve the read alignment more for the repeat regions than the non-repeat regions. However, longer read lengths would increase the sequencing cost. Therefore a balance between the sequenced read length and sequencing needs to be considered.

By allowing the mismatches in the index sequences and read alignment, the number of average aligned reads increased by 0.098 million, 0.47 million and 0.10 million for 1 mismatch allowable in the index sequence, one and two mismatches allowable in the read alignment, respectively. However the CVs of measuring chr13 and chr18 were slightly worse when more mismatches were allowed in the index sequence or read alignment. This was due to the errors that were introduced in sorting back the reads to the samples and aligning the reads to the reference genome. However, unlike allowing the mismatches in the read alignment, allowing mismatch in the index sequences helped to increase the number of aligned reads of a few samples with extremely low aligned reads, which might be possibly due to the errors in the readout of index sequences. Therefore it was reasonable to allow mismatches in the index sequence but no mismatches in the read alignment.

After the improvement of the alignment, the detection rate for trisomy 13 and 18 was 44.0% and 83.8%. Although the detection rate was better than that based on the T21 bioinformatics analysis pipeline, it was still not compatible to the detection rate for trisomy 21 by NGS. On the other hand, it had been observed that there was a correlation between the average GC content of the autosomes and the precision of quantifying the autosomes. The autosomes with high or low average GC content had relatively large CV. This indicated that the GC content was a factor that affected the precision of quantifying the autosomes. This will be discussed in the following sections.

II. Reducing the GC Bias by Correction of Read Counts

A second step of the bioinformatics analysis pipeline is the quantification of chromosomes by counting the aligned reads in the sequencing data.

Theoretically, if there was no bias in NGS platform, it would be expected that the sequenced reads from NGS platform should be uniformly distributed across the genome. However, it has been reported that the sequenced reads from different regions were not uniquely distributed. The guanine and cytosine (GC) content of the sequenced nucleic acids has been reported to contribute to the non-uniform distribution. For example, it has been found that there was a positive correlation between the GC content and the number of sequenced reads across the genome on Illumina sequencing platform. There was a relatively low sequencing coverage in the GC-poor regions and high sequencing coverage in the GC-rich regions. This "GC bias" was probably introduced in the PCR steps during the sequencing procedures. However, whether this GC bias existed in the plasma DNA sequencing data needs further validation.

It is likely that this GC bias would affect the quantification of chr13 and chr18 by NGS in two aspects. First, due to GC bias, the read counts from each chromosome was not only correlated to the mount of sequenced DNA molecules derived from the corresponding chromosome, but also correlated to the GC content of that chromosome. Therefore, the number of DNA molecules from each chromosome could not be precisely measured by the read counts from the sequencing data. Second, due to the GC content difference between the individual chromosome and the whole genome, the degree of the GC bias for individual chromosome and the whole genome was different. Therefore the proportion of the reads derived from certain chromosomes over the total reads from the whole genome (genomic representation of this chromosome) could not be precisely calculated. Algorithms that could reduce the GC bias in these two aspects might improve the performance of the trisomy 13 and 18 detection by NGS.

This section determines whether the GC bias exists in the plasma sequencing data and whether this GC bias would affect the precision of quantifying chr13 and chr18. In order to reduce the GC bias, an algorithm that directly corrected the GC bias in read counts was developed. The performance of the trisomy 13 and 18 detection by NGS was then accessed after reducing the GC bias. Another algorithm that reduced the effect of GC bias in the calculation of genomic representation will be discussed in the next section.

Sequenced reads were aligned to the non-repeat masked human reference genome with no mismatch allowable. After alignment, the reads were sorted back to the corresponding sample with one mismatch allowable in the index sequence.

The sequence of whole genome (Hg18 NCBI.36) was first divided into consecutive 50 kilobases (kb) segments, termed bins. The GC content of each bin was calculated by calculating the percentage of G+C nucleotide counts over A+T+C+G nucleotide counts. The 'N's in the genomic sequence were not considered. The reads falling in each bin were counted. The correlation between the GC content and the read counts in bins was calculated by Spearman's Rank Correlation Coefficient with R.

In order to reduce the GC bias, an algorithm was implemented to correct such bias in the read counts. For each sample, the whole genome sequence was first divided into 50 kb bins. The bin size of 50 kb was arbitrarily chosen and it will be discussed later. The number of aligned reads and GC content in each bin (rounded to 0.1%) were then calculated. Bins without any reads and bins with 'N' in the sequences were excluded. Then, the number of aligned reads in each bin against the GC content of the corresponding bin was fit by either linear regression or locally weighted scatterplot smoothing (LOESS) regression. The regression fit predicted value for each bin (P) could be calculated after regression by using the regression function and the GC content of each bin. For each bin, the GC corrected read counts ($RC_1$) were calculated based on the raw read counts with the correction factor (F). The median count of all bins (M) was used as the correction reference. The GC-corrected read counts were calculated by the following equations:

$$F=M/P$$

$$RC_{GC}=RC_{raw} \times F$$

Instead of directly using the counts of aligned read, the GC-corrected read count was then used to calculate the genomic representations.

GC Bias

Figure 3A:
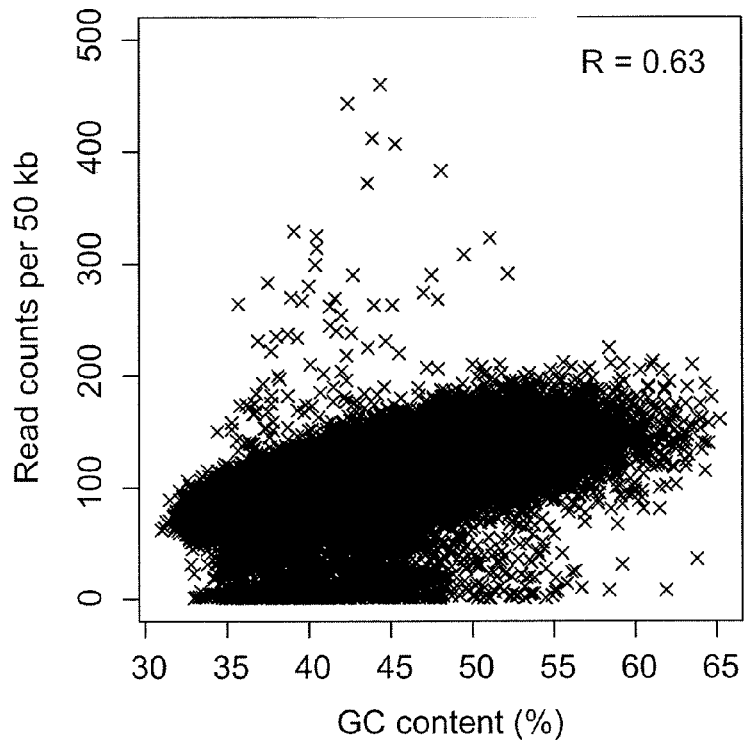
FIG. 3A. The correlation between the GC contents and the read counts in the plasma DNA sequencing data before GC correction. Scatter plot of the GC contents and read counts per 50 kb bins of the plasma DNA sequencing data from a euploid sample before GC correction. The Spearman's Rank Correlation Coefficient was showed. Outliers were not plotted.

First, whether the GC bias existed in the plasma DNA sequencing data was checked. By calculating the correlation between the GC content and the read count with 50 kb bins, a positive correlation had been observed (the average correlation coefficient for all the samples are 0.56, SD=0.13) (FIG. 3A). Thus the GC bias did exist in the plasma DNA sequencing data.

From previous analysis (FIG. 2B), the chromosomes with low or high GC content tend to have greater variance than those with modest GC content. Thus, chr13, chr18 and chr21 with average GC content 38.52%, 39.79% and 40.88% had the CVs of 1.12%, 0.67% and 0.55% with improved alignment, respectively. These results showed that chr13 and chr18, which had relatively lower GC content than chr21, were less precisely measured. These result indicated that the GC bias affected the precision of measuring the GR of chromosomes, especially those chromosomes with high or low average GC content. Thus the GC bias needed to be reduced in order to improve the performance of the trisomy 13 and 18 detection by NGS.

Correcting the GC Bias in Read Counts by Linear Regression

One of the possible solutions to reduce the GC bias is to directly correct such bias in read counts. Since there was a correlation between the GC contents and the read counts, eliminating this correlation would potentially reduce the GC bias and improve the performance for trisomy 13 and 18 detection. To test this, a GC correction algorithm with linear regression was implemented to eliminate the correlation. The linear regression was used to characterize the correlation between the GC contents and read counts in 50 kb bins. Theoretically, if there was no such correlation, the read counts per bin would be expected to be close to the median count of all bins. Therefore, the median count of all bins was used as the correction reference and the read counts in each bin were normalized to the correction reference.

Figure 3B:
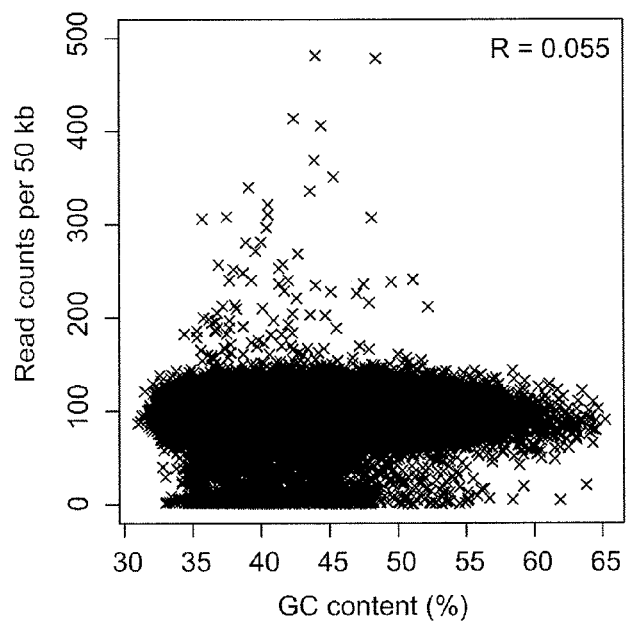
FIG. 3B. The correlation between the GC contents and the read counts in plasma DNA sequencing data after GC correction with linear regression. Scatter plot of the GC contents and read counts per 50 kb bins of the plasma DNA sequencing data from a euploid sample after GC correction with the linear regression. The Spearman's Rank Correlation Coefficient was showed. Outliers were not plotted.
Figure 3C:
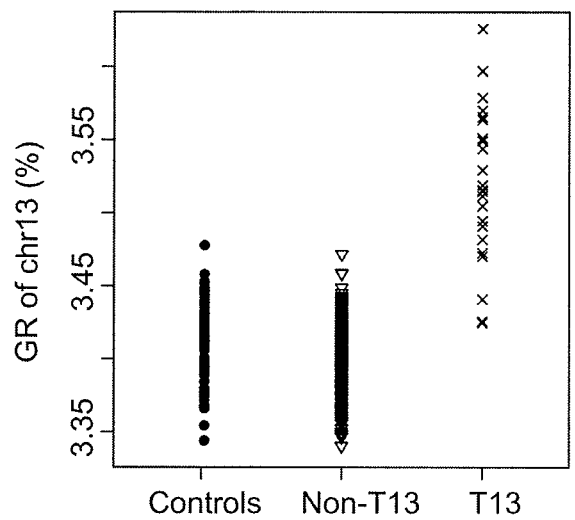
FIGS. 3C and 3D. Trisomy 13 detection after GC correction with linear regression. The GC correction with linear regression was performed. (C) The genomic representation of chr13 after GC correction with linear regression was calculated for the trisomy 13, non-trisomy 13 and reference control samples (D) Z score of chr13 was calculated for the trisomy 13, non-trisomy 13 and reference control samples. Dashed line indicated the diagnostic cutoff with a z score value of 3. T13, trisomy 13. GR, genomic representation.

After the GC correction, the average correlation coefficient for all the samples was 0.14 (SD=0.018) (FIG. 3B). This indicated that the correlation between GC-corrected read counts and GC contents in each bin had been greatly reduced after GC correction with linear regression, although a slightly small correlation still existed. As shown in Table 5.1, the CVs of measuring chr13 and chr18 decreased from 1.124% and 0.647% to 0.426% and 0.331%, respectively, after GC correction. These results indicated that the precision of quantifying chr13 and chr18 by NGS had been improved by GC correction with the linear regression.

TABLE 5.1

CVs of quantifying autosomes before and after GC correction with linear regression.

| | CVs | |
|---|---|---|
| Chromosome | No GC correction | GC correction with linear regression |
| chr4 | 1.423% | 0.346% |
| chr13 | 1.124% | 0.426% |
| chr5 | 0.799% | 0.276% |
| chr6 | 0.723% | 0.231% |
| chr3 | 0.663% | 0.266% |
| chr18 | 0.674% | 0.331% |
| chr8 | 0.528% | 0.282% |
| chr2 | 0.338% | 0.183% |
| chr7 | 0.425% | 0.269% |
| chr12 | 0.343% | 0.326% |
| chr21 | 0.546% | 0.532% |

TABLE 5.1-continued

CVs of quantifying autosomes before and
after GC correction with linear regression.

| Chromosome | CVs | |
| --- | --- | --- |
| | No GC correction | GC correction with linear regression |
| chr14 | 0.316% | 0.333% |
| chr9 | 0.416% | 0.303% |
| chr11 | 0.454% | 0.252% |
| chr10 | 0.572% | 0.328% |
| chr1 | 0.519% | 0.259% |
| chr15 | 0.895% | 0.617% |
| chr20 | 1.533% | 0.366% |
| chr16 | 1.614% | 0.480% |
| chr17 | 2.140% | 0.343% |
| chr22 | 3.355% | 0.503% |
| chr19 | 2.886% | 1.089% |

Chromosomes are order from top to bottom in increasing GC contents.

Figure 3D:
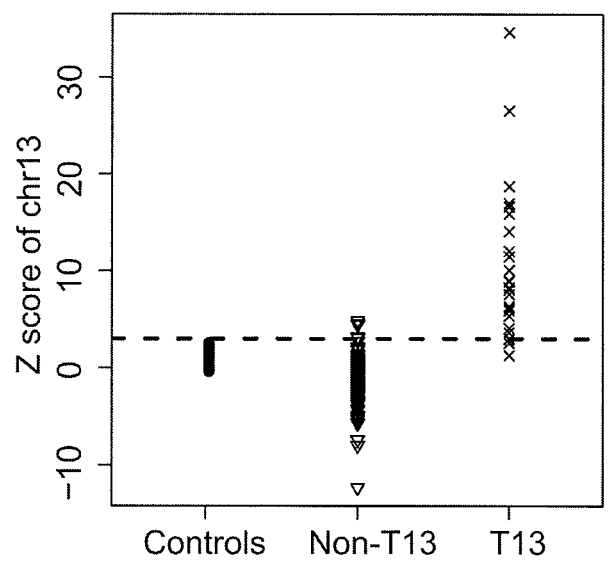
Figure 3E:
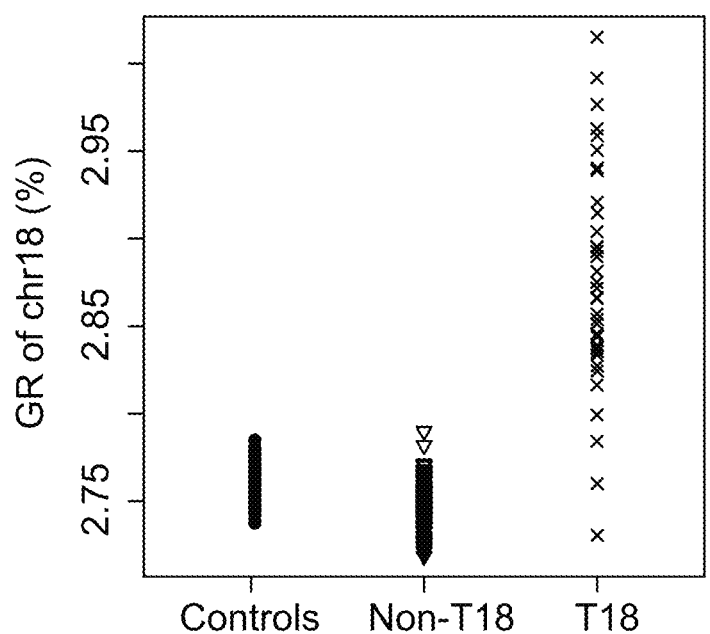
FIGS. 3E and 3F. Trisomy 18 detection after GC correction with linear regression. The GC correction with linear regression was performed. (A) Genomic representation of chr18 after GC correction with linear regression was calculated for the trisomy 18, non-trisomy 18 and reference control samples (B) Z score of chr18 was calculated for the trisomy 18, non-trisomy 18 and reference control samples. Dashed line indicated the diagnostic cutoff with a z score value of 3. T18, trisomy 18. GR, genomic representation.
Figure 3F:
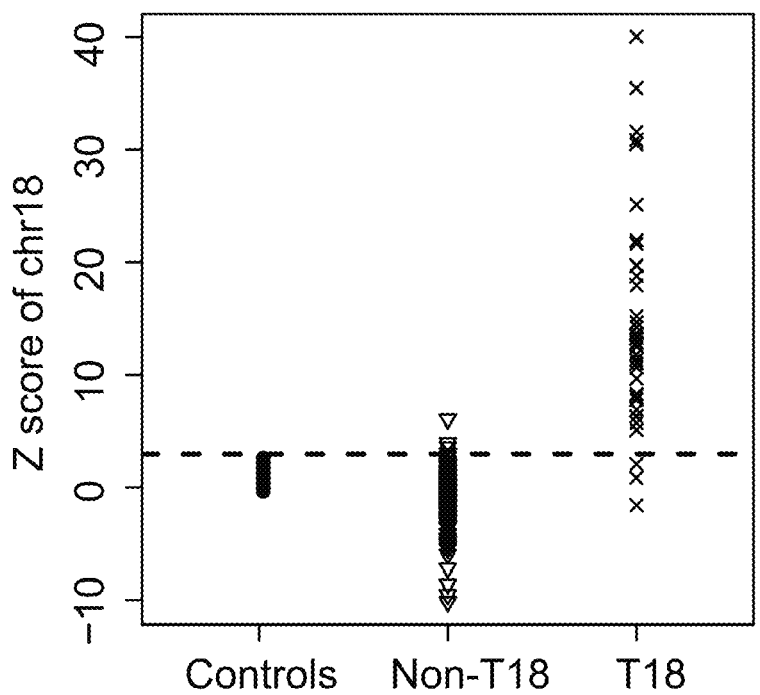

Next, the performance of the trisomy 13 and 18 detection after GC correction with the linear regression was assessed. When using the diagnostic z-score value of 3 as the cutoff, 22 out of 25 trisomy 13 cases and 259 out of 264 non-trisomy 13 cases were successfully identified (FIG. 3D). The sensitivity and specificity were thus 88.0% and 98.1%. For trisomy 18, 34 out of 13 trisomy 37 cases and 247 out of 252 non-trisomy 18 cases were correctly identified, corresponding to a sensitivity and specificity of 91.9% and 98.0% (FIGS. 3E and 3F). These results indicated that the trisomy 13 and 18 detection had been improved by the GC correction algorithm.

Correcting the GC Bias in Read Counts by Non-linear Regression

In the previous analysis, the correlation between the GC contents and read counts was considered as the linear relation and the linear regression was used to fit this correlation. However, a slightly small correlation between the GC contents and read counts still existed after the linear regression (average correlation is 0.14, SD=0.018). It is possible that the linear regression was not good enough to fit such a correlation. Therefore, a non-linear regression, LOESS regression, was used in the GC correction algorithm to fit this correlation.

Figure 4A:
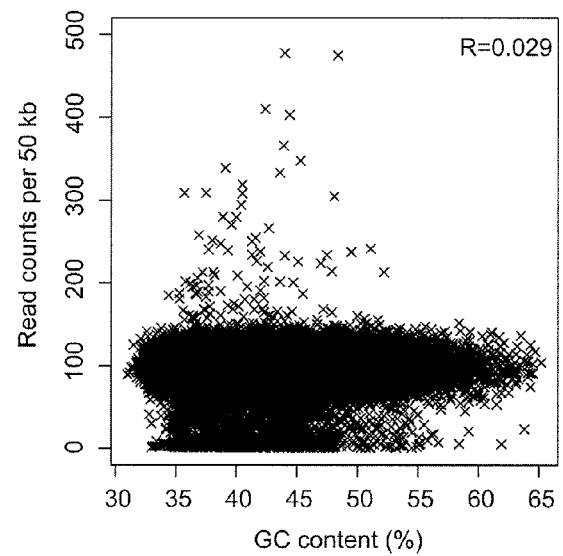
FIG. 4A. The correlation between the GC contents and the read counts in plasma DNA sequencing data after GC correction with LOESS regression. Scatter plot of the GC contents and read counts per 50 kb bins of the plasma DNA sequencing data from a euploid sample after GC correction with the LOESS regression. The Spearman's Rank Correlation Coefficient was showed. Outliers were not plotted.
Figure 4B:
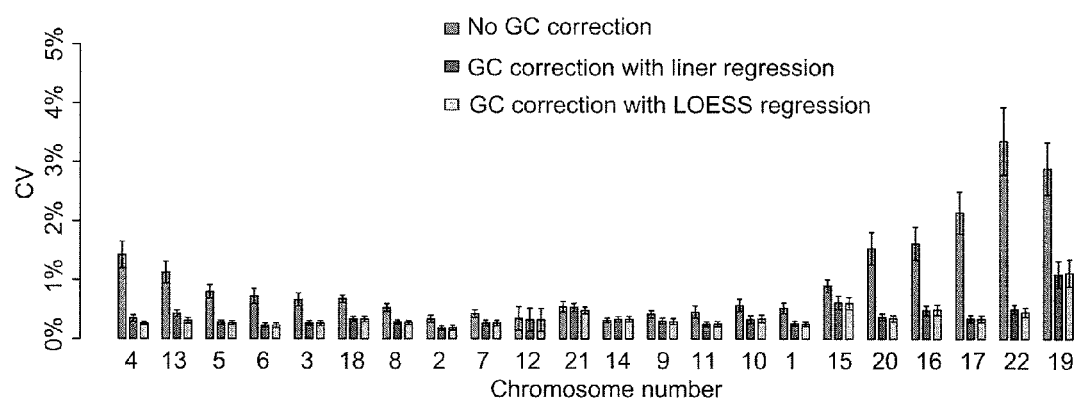
FIG. 4B. The precision of quantifying autosomes with and without GC correction. CVs of quantifying autosomes among control samples were plotted. CVs calculated with or without GC correction were plotted in different colors. The chromosomes were ordered from left to right in increasing GC contents.
Figure 5A:
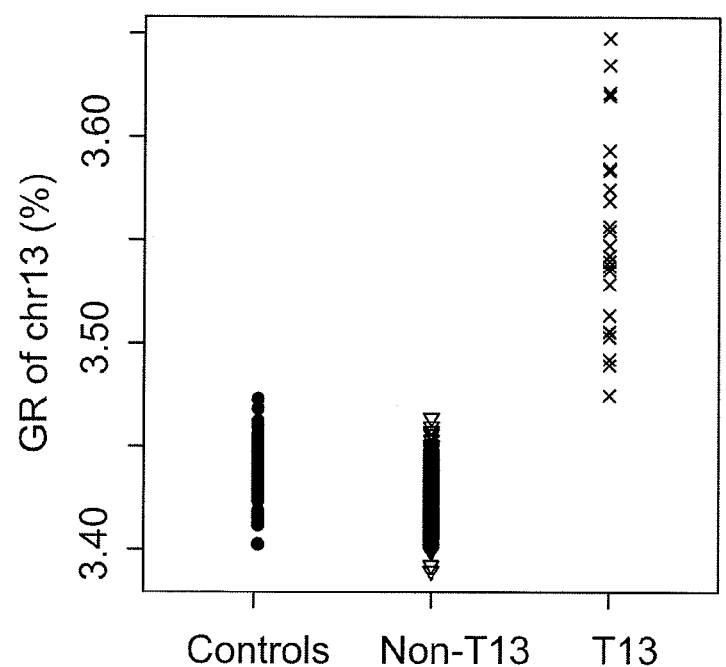
FIGS. 5A and 5B. Trisomy 13 detection after GC correction with LOESS regression. The GC correction with LOESS regression was performed. (A) Genomic representation of chr13 after GC correction with LOESS regression was calculated for the trisomy 13, non-trisomy 13 and reference control samples (B) Z score of chr13 was calculated for the trisomy 13, non-trisomy 13 and reference control samples. Dashed line indicated the diagnostic cutoff with a z-score of 3. T13, trisomy 13. GR, Genomic representation.
Figure 5B:
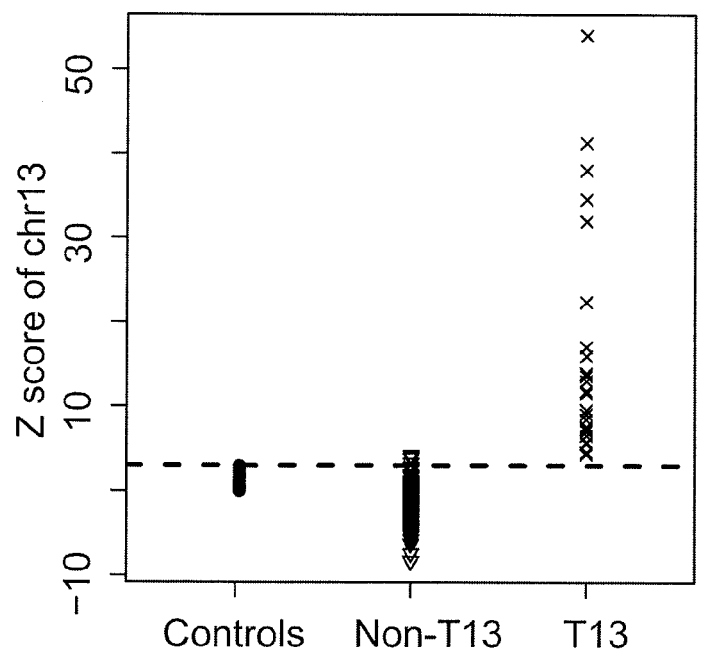
Figure 5C:
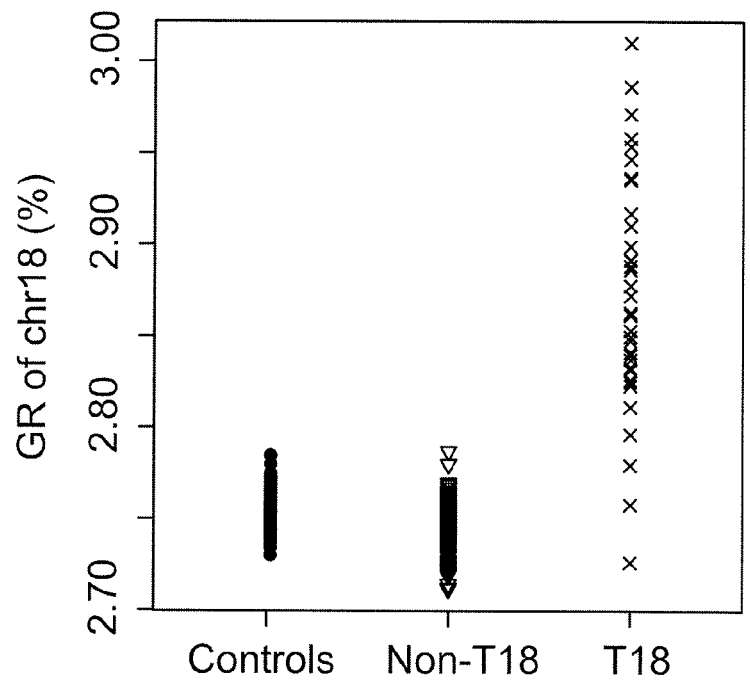
FIGS. 5C and 5D. Trisomy 18 detection after GC correction with LOESS regression. The GC correction with LOESS regression was performed. (C) Genomic representation of chr18 after GC correction with LOESS regression was calculated for the trisomy 18, non-trisomy 18 and reference control samples (D) Z score of chr18 was calculated for the trisomy 18, non-trisomy 18 and reference control samples. Dashed line indicated the diagnostic cutoff with a z-score of 3. T18, trisomy 18. GR, Genomic representation.
Figure 5D:
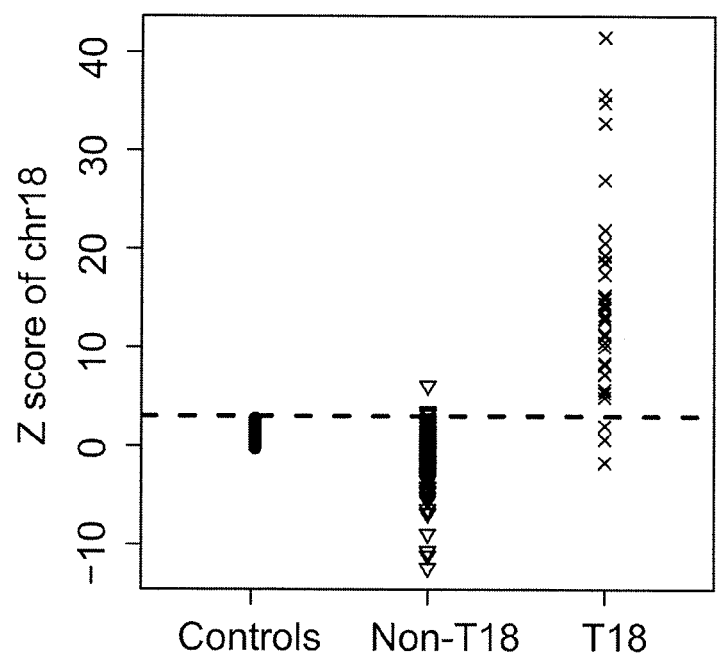

After the GC correction with LOESS regression, the average correlation coefficient for all the samples are 0.02 (SD=0.004) (FIG. 4A). Compared to the results with linear regression, the correlation was smaller and there was almost no correlation between the GC contents and read counts after the GC correction with LOESS regression. Furthermore, the CVs of measuring chr13 decreased to 0.31%. CVs after the GC correction with LOESS regression was smaller than that with linear regression (FIG. 4B and Table 5.2). This result indicated that the precision of quantifying chr13 had been improved more by GC correction with the LOESS regression. For the precision measuring chr18, the CVs slightly increased to 0.334% by 0.003%.

TABLE 5.2

CVs of quantifying autosomes before and after GC
correction with linear regression and LOESS regression.

| Chromosome | CVs | | |
| --- | --- | --- | --- |
| | No GC correction | GC correction with linear regression | GC correction with LOESS regression |
| chr4 | 1.423% | 0.346% | 0.262% |
| chr13 | 1.124% | 0.426% | 0.310% |

TABLE 5.2-continued

CVs of quantifying autosomes before and after GC
correction with linear regression and LOESS regression.

| Chromosome | CVs | | |
| --- | --- | --- | --- |
| | No GC correction | GC correction with linear regression | GC correction with LOESS regression |
| chr5 | 0.799% | 0.276% | 0.267% |
| chr6 | 0.723% | 0.231% | 0.229% |
| chr3 | 0.663% | 0.266% | 0.265% |
| chr18 | 0.674% | 0.331% | 0.334% |
| chr8 | 0.528% | 0.282% | 0.276% |
| chr2 | 0.338% | 0.183% | 0.189% |
| chr7 | 0.425% | 0.269% | 0.269% |
| chr12 | 0.343% | 0.326% | 0.324% |
| chr21 | 0.546% | 0.532% | 0.480% |
| chr14 | 0.316% | 0.333% | 0.334% |
| chr9 | 0.416% | 0.303% | 0.295% |
| chr11 | 0.454% | 0.252% | 0.252% |
| chr10 | 0.572% | 0.328% | 0.340% |
| chr1 | 0.519% | 0.259% | 0.251% |
| chr15 | 0.895% | 0.617% | 0.604% |
| chr20 | 1.533% | 0.366% | 0.346% |
| chr16 | 1.614% | 0.480% | 0.491% |
| chr17 | 2.140% | 0.343% | 0.339% |
| chr22 | 3.355% | 0.503% | 0.450% |
| chr19 | 2.886% | 1.089% | 1.116% |

* Chromosomes are order from top to bottom in increasing GC contents.

The performance of the trisomy 13 and 18 detection after GC correction with the LOESS regression was assessed. When using the diagnostic z-score value of 3 as the cutoff, all the trisomy 13 cases (25 out of 25) and 261 out of 264 non-trisomy 13 cases were successfully identified. The sensitivity and specificity were thus 100% and 98.9%. Compared with the GC correction with linear regression, the performance of the trisomy 13 detection had been improved after the GC correction with LOESS regression. For trisomy 18, 34 out of 37 trisomy 18 cases and 247 out of 252 non-trisomy 18 cases were correctly identified, corresponding to a sensitivity and specificity of 91.9% and 98.0%. There was no markedly improvement in the performance for trisomy 18 detection, when comparing the GC correction methods with two different regression models.

Bin Size

Figures 6A, 6B:
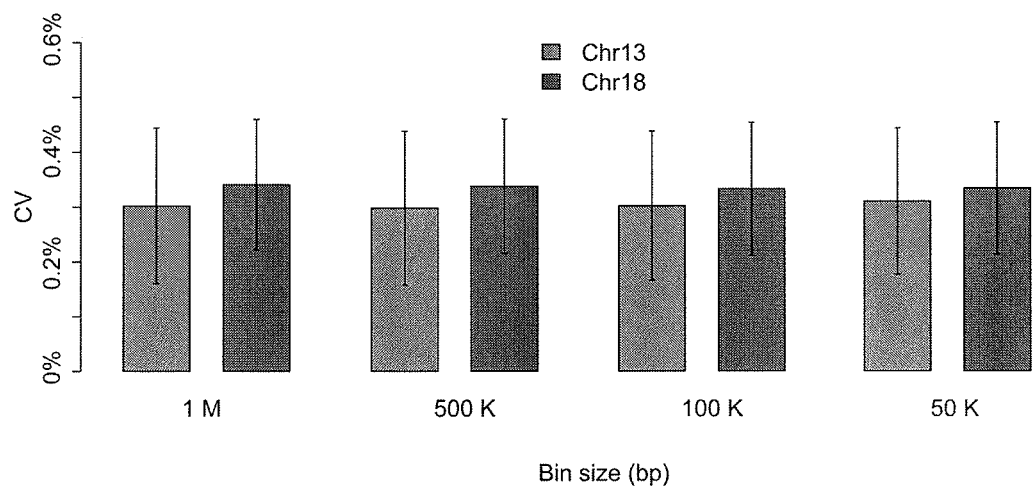
FIG. 6A. CVs of measuring chr13 and chr18 by GC correction with different bin sizes. Different bin sizes were used to perform the GC correction. M, megabases. K, kilobases. After GC correction, the CVs of quantifying chr13 and chr18 among the control samples were calculated.
FIG. 6B. CVs for quantifying chr13 and chr18 among control samples by GC correction with different bin size. M, megabases. K, kilobases. GR, genomic representation.
Figure 6C:
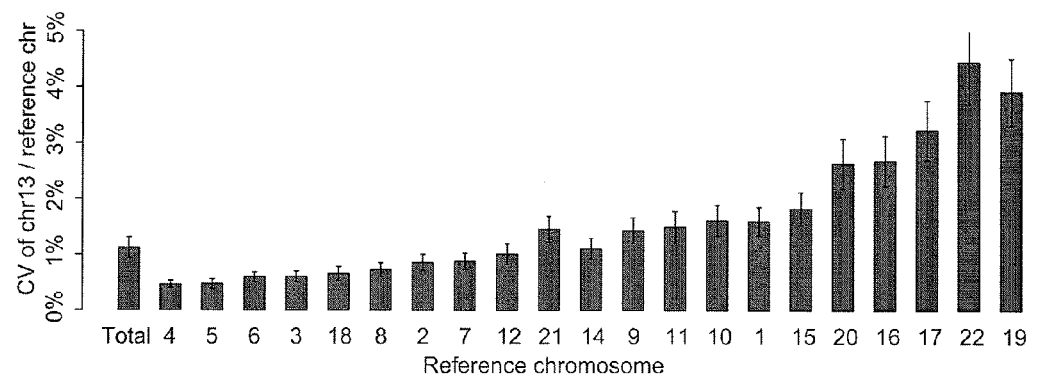
FIGS. 6C and 6D. CVs of quantifying chr13 and chr18 by using different reference chromosomes. CVs of modified GR of (C) chr13 and (D) chr18 by using different reference chromosomes. Total, total chromosomes (whole genome).
Figure 6D:
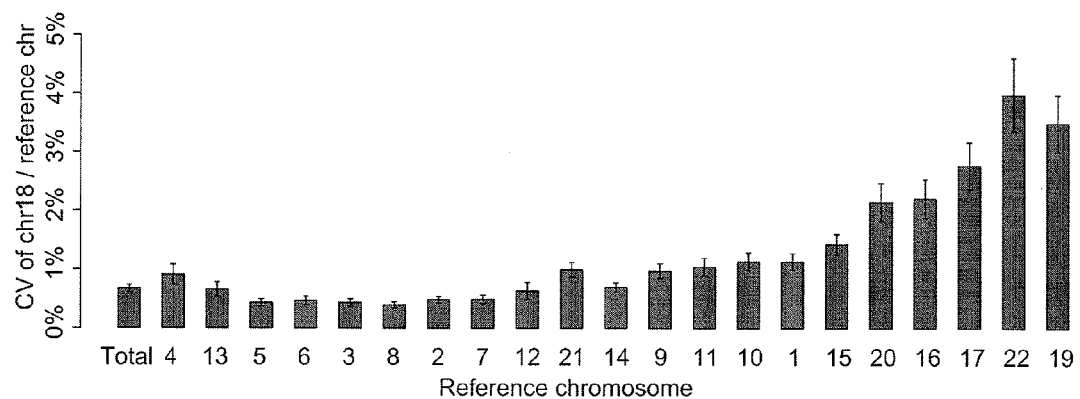
Figure 6E:
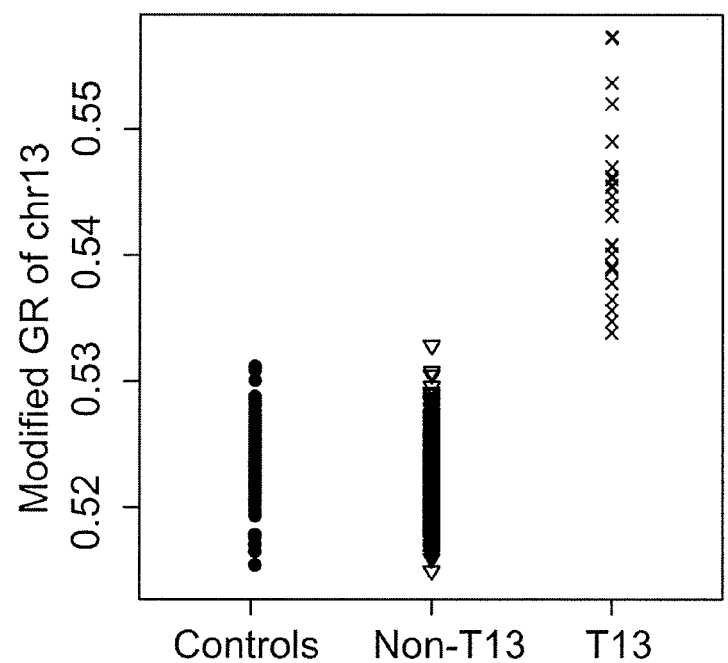
FIGS. 6E and 6F. Trisomy 13 detection by using modified genomic representation calculation. (E) Modified genomic representation of chr13 was calculated for the trisomy 13, non-trisomy 13 and reference control samples. Chr4 was used as the reference chromosome to calculate the GR of chr13 (F) The z score of chr13 by using the modified genomic representation was calculated for the trisomy 13, non-trisomy 13 and reference control samples. Dashed line indicated the diagnostic cutoff with a z-score of 3. T13, trisomy 13. GR, genomic representation.
Figure 6F:
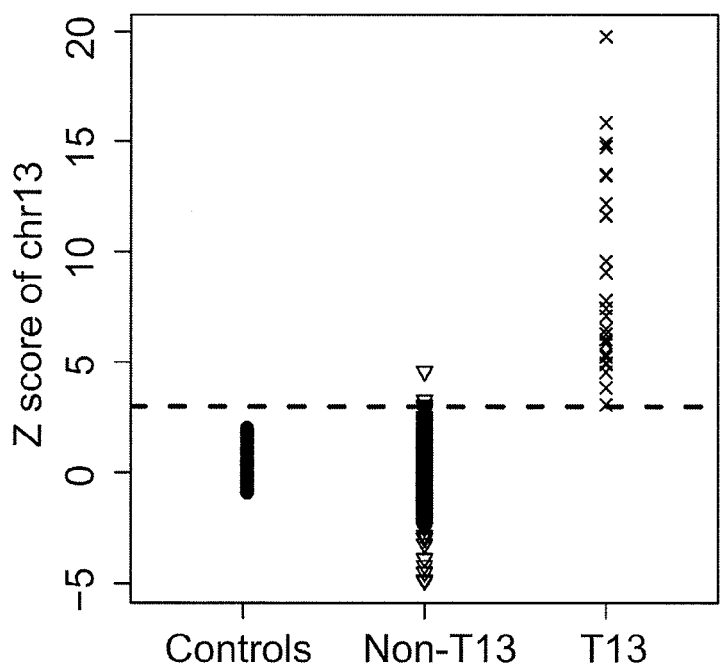
Figure 6G:
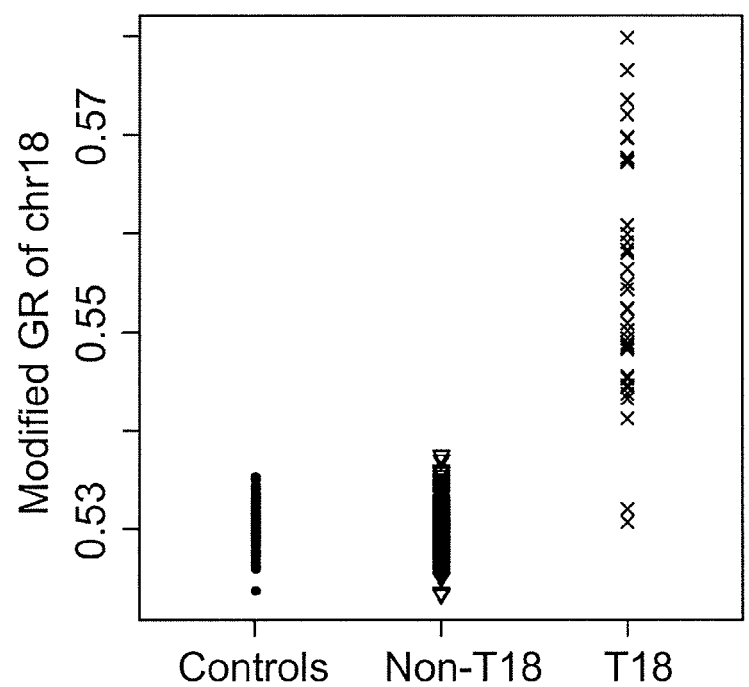
FIGS. 6G and 6H. Trisomy 18 detection by using modified genomic representation calculation. (G) Modified genomic representation of chr18 was calculated for the trisomy 18, non-trisomy 18 and reference control samples. Chr8 was used as the reference chromosome to calculate the GR of chr18 (H) The z score of chr18 by using the modified genomic representation was calculated for the trisomy 18, non-trisomy 18 and reference control samples. Dashed line indicated the diagnostic cutoff with a z-score of 3. T18, trisomy 18. GR, genomic representation.
Figure 6H:
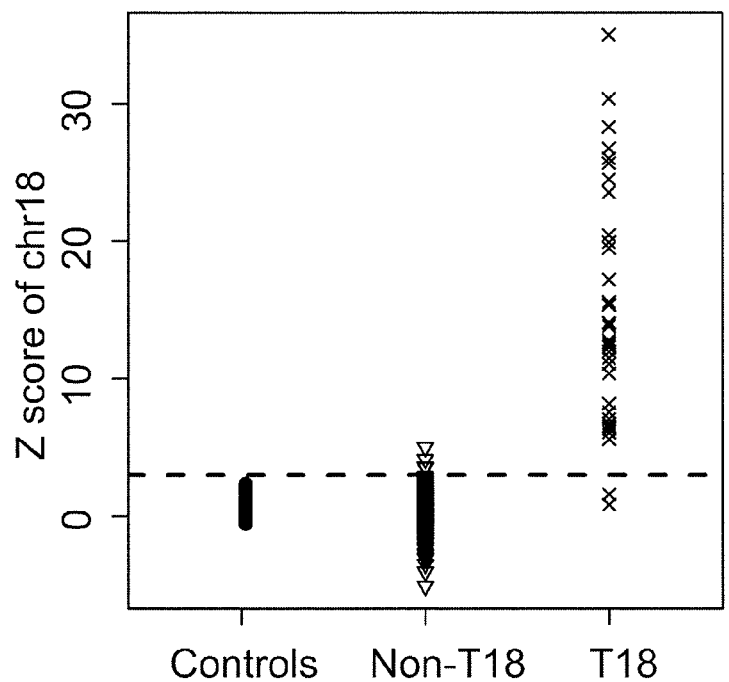
Figures 7A, 7B:
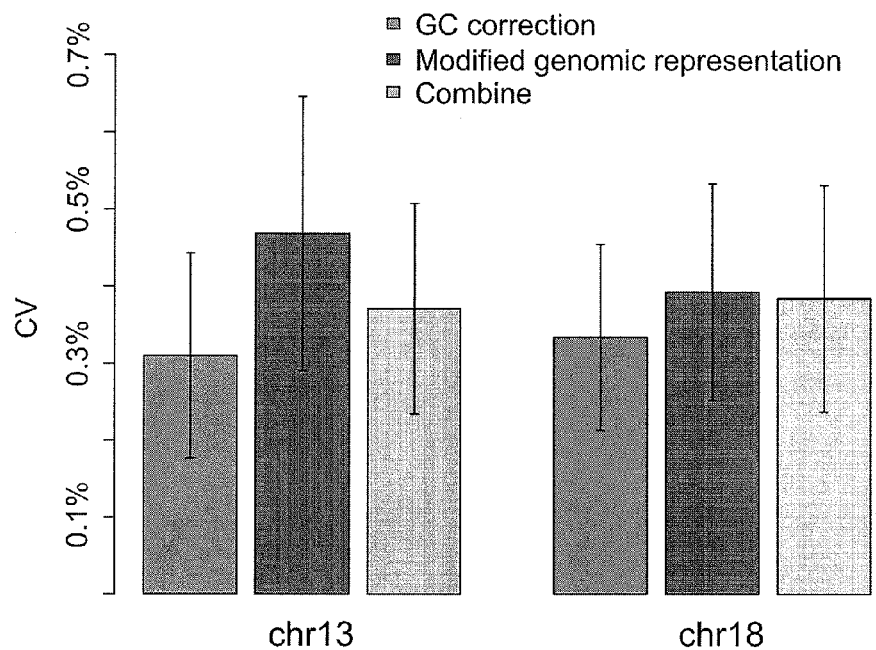
FIG. 7A. The precision of quantifying chr13 and chr18 by different GC bias reduction methods. CVs of quantifying chr13 and chr18 by GC correction, modified genomic representation or combining these two methods.
FIG. 7B. CVs of quantifying chr13 and chr18 by different GC bias reduction methods.

In order to assess the effect of bin size in the GC correction algorithm, a series of bin size 1 mb, 500 kb, 100 kb and 50 kb were tested. The results showed no marked difference in CVs among different bin sizes (FIG. 6A and Table 5.4). However, when the bin size became smaller, the time for computing the LOESS regression dramatically increased. For example, when the bin size was 50 kb, the average time to perform the GC correction on one sample was longer than five hours on a computing server with an Intel® Xeon® CPU X5570 2.93 GHz and 36 G memory. In order to save the computing time, a 500 kb bin size was used in the following analysis.

In this section, GC bias had been confirmed to exist in the plasma DNA sequencing data and contributed to the imprecision of quantifying chr13 and chr18 by NGS. In order to reduce such a bias, a GC correction algorithm with linear or non-linear (LOESS) regression had been implemented to correct such bias in read counts. After GC correction, the performance for trisomy 13 and 18 detection had been improved.

The GC correction improved the precision of quantifying chr13 and chr18 by NGS. Compared with the previous results without GC correction, the CVs of quantifying chr13 and chr18 decreased by up to 72.4% and 50.9%, respectively, after the GC correction. The detection rate also increased from 44% to 100% for trisomy 13 and 83.8% to 91.9% for trisomy 18. The improvement for trisomy 13 was more prominent than that for trisomy 18. This was probably due to the greater deviation in the average GC content for chr13 (38.5%) than that for chr18 (39.8%) compared with the average GC contents of the whole genome (41.7%). These results indicated that the degrees of GC bias in chr13, chr18 and whole genome were different. Moreover, the genomic representation of chr13 and chr18 was calculated by using the whole genome as the reference. It was possible that using the chromosome with similar GC contents with chr13 or chr18, instead of whole genome, as the reference to calculate the GR of chr13 or chr18 might counteract the GC bias. This will be further discussed in the following section.

Compared with the linear regression in the GC correction, the CVs of quantifying chr13 decreased by 27% and the detection rate for trisomy 13 increased from 88.0% to 100% by using the non-linear (LOESS) regression. There was no marked difference for the quantification of chr18 or the detection of trisomy 18 by the two different regression models in the GC correction. Nevertheless, the overall performance of the LOESS regression in the GC correction was better than the linear regression. Therefore, the GC correction with LOESS regression will be adapted for the following analysis.

The bin size parameter used in the GC correction algorithm was discussed in this section. By calculating the CVs of quantifying chr13 and chr18, it showed that this parameter had little influence on the performance of the GC correction algorithm at current sequencing depth. These results demonstrated that the GC correction was quite robust at current sequencing depth since the performance was not significantly changed with different parameters. However, in the current sequencing depth, the CVs of quantifying chr13 and chr18 were already quite low after GC correction. Therefore changing the parameters used in the GC correction algorithm might not significantly affect its performance. Thus, when applying the GC correction algorithm, one did not need to pay specifically attention to the parameters in the GC correction with enough sequencing depth (for example, more than four million reads per sample).

The GC bias pattern might change with different sequencing platform and reaction reagents. For example, Illumina has updated its sequencing platform and also improved the sequencing reagents in order to reduce the GC bias. Therefore, the parameters used in the GC correction algorithm needs may be modified on different sequencing platforms and reagent versions.

III. Reducing GC Bias by Modifying Genomic Representation Calculation

In a second step of the bioinformatics analysis pipeline, another part of quantifying chromosome can be to calculate the genomic representation after counting the reads for each chromosome. This might be further improved.

It has been discussed in the previous section that the GC bias would possibly affect the detection of trisomy 13 and 18 in two aspects: one is the read counts and the other is the genomic representation. It has been found that the degree of GC bias for chr13, chr18 and whole genome is different due to their different average GC content. It also has been suspected that using the whole genome as the reference to calculate the GR of chr13 and chr18 might not be accurate due to the different GC effect. Using other reference chromosomes that have the similar GC contents with chr13 and 18 to calculate the GC of these two chromosomes might counteract the GC effect. This might be another alternative method to reduce the GC bias effect, independently from the GC correction of read counts.

Reducing the GC Bias by Modifying Genomic Representation Calculation

Since GC bias affects the precision of measuring genomic representation of chr13 and chr18, one possible way to reduce the GC bias is to modify the calculation of the genomic representation of chr13 and chr18. The original genomic representation for chr13 or chr18 was calculated by the read counts from chr13 or chr18 over the read counts from all chromosomes (whole genome). However, the average GC contents of chr13 or chr18 and whole genome are different. This difference might contribute to the imprecision of calculating the GR.

To test this hypothesis, other chromosomes as reference were used to calculate the GR of chr13 and chr18. CVs of the original GR of chr13 and chr18 were 1.124% and 0.674%, respectively. When using chr4 and chr8 as the reference to calculate the modified GR for chr13 and chr18, respectively, the CVs increased to 0.468% and 0.393%. The average GC contents of chr13 and chr18 were 38.5% and 39.8%. The chr4 (GC %=38.2%) and chr8 (GC %=40.2%) had very similar average GC contents to chr13 and chr18 respectively.

After calculating the modified genomic representation of chr13 and chr18, the standard z score approach was used to classify the trisomy samples. 25 out 25 trisomy 13 cases and 261 out of 264 non-trisomy 13 cases were correctly identified, corresponding to a sensitivity and specificity 100% and 98.9%, respectively. For trisomy 18, 35 out of 37 trisomy 18 cases and 247 out of 252 non-trisomy 18 cases were identified correctly, corresponding to a sensitivity and specificity 94.6% and 98.0%, respectively.

TABLE 6.1

CVs of modified GR of chr13 and chr18 by using different reference chromosomes.

| Reference chr | Average GC contents (%) | CVs of chr13/ reference chr (%) | CVs of chr18/ reference chr (%) |
|---|---|---|---|
| chr4 | 38.218 | 0.468 | 0.914 |
| chr13 | 38.520 | — | 0.659 |
| chr5 | 39.519 | 0.474 | 0.432 |
| chr6 | 39.600 | 0.596 | 0.468 |
| chr3 | 39.691 | 0.606 | 0.433 |
| chr18 | 39.785 | 0.659 | — |
| chr8 | 40.167 | 0.729 | 0.393 |
| chr2 | 40.236 | 0.862 | 0.482 |
| chr7 | 40.738 | 0.881 | 0.490 |
| chr12 | 40.804 | 1.013 | 0.636 |
| chr21 | 40.878 | 1.459 | 1.001 |
| chr14 | 40.887 | 1.108 | 0.699 |
| chr9 | 41.317 | 1.437 | 0.977 |
| chr11 | 41.566 | 1.498 | 1.048 |
| chr10 | 41.585 | 1.613 | 1.134 |
| chr1 | 41.743 | 1.595 | 1.136 |
| chr15 | 42.205 | 1.823 | 1.431 |
| chr20 | 44.126 | 2.630 | 2.153 |
| chr16 | 44.789 | 2.682 | 2.213 |
| chr17 | 45.531 | 3.226 | 2.776 |
| chr22 | 47.983 | 4.450 | 3.987 |
| chr19 | 48.364 | 3.913 | 3.496 |
| Whole genome | 41.679 | 1.124 | 0.674 |

The chromosomes were ordered by their average GC contents from high GC contents to low.

Combining GC Correction and Modified Genomic Representation

Two independent methods, GC correction and modified genomic representation, had been developed to reduce the GC bias in the sequencing data. Both of these two methods had greatly improved the detection accuracy for trisomy 13 and 18. Above, these two methods were independently used in the analysis pipeline. Here, the methods are combined.

The read counts were corrected by GC correction with LOESS regression as described in section 5. The bin size was 500 kb. After the GC correction, the corrected read counts were used to calculate the modified genomic representation. For chr13 and chr18, chr4 and chr8 were used as the reference chromosomes, respectively. CVs of quantifying chr13 and chr18 were then assessed.

After combining the two GC bias reduction methods, the CVs of quantifying chr13 and chr18 were 0.371% and 0.384%, respectively. The precision of quantifying chr13 and chr18 by combining these two methods were worse than that by GC correction, but better than that by modified genomic representation. These results indicated that the performance of combining these two methods was no better than that of GC correction alone.

In this section, another independent method was developed to reduce the GC bias in the genomic representation calculation, besides the GC correction. Chr4 and chr8 were used as the reference chromosomes for chr13 and chr18, respectively, to calculate the modified genomic representation. Compared with the results using original genomic representation calculation, the CVs for quantifying chr13 and chr18 increased from 1.12% to 0.47% and 0.67% to 0.39%, respectively. CVs for quantifying chr13 and chr18 had been improved by 58.2% and 41.3%, respectively. The detection rate increased from 44.0% to 100% for trisomy 13 and 83.8% to 98.0% for trisomy 18.**

Comparing GC correction method and modified GR method, the CVs for quantify chr13 were 0.310% and 0.468%, respectively. For chr18, the CVs were 0.334% and 0.393%. These results indicated that the GC correction method outperformed the modified GR method. However, the performance for trisomy 13 and 18 detection based on these two GC bias reducing method were similar in current sequencing depth. Both of the methods greatly improved the precision of measuring chr13 and chr18 and also improved the performance for trisomy 13 and 18 detection. Nevertheless, it would be expected when the sequencing depth was low, the GC correction method would have a better performance than the modified GR method.

The GC correction method and modified GR method were independently used to reduce the GC bias. Whether these two methods could be combined to reduce the GC bias is unclear. Therefore, the two independent GC bias reduction methods have been combined and tested. The results showed that the precision of quantifying chr13 and chr18 by combining these two methods was worse than that by GC correction alone, but better than that by modified genomic representation alone. Although these two methods reduced the GC bias in two different aspects independently, one in the read counts, the other in the genomic representation calculation, the performance of combining these two methods was suboptimal. This was probably because that after GC correction, the pattern of GC bias was different for chr13 and chr4 or chr18 and chr8. Therefore using chr4 and chr8 as the reference to calculate the modified genomic representation for chr13 and chr18 was not appropriate. Since the GC correction was the best method for reducing the GC bias, it will be adapted for the following analysis.

IV. Improving the Statistics for Trisomy Detection

A third part for improvement in the analysis pipeline is the statistics for trisomy (e.g. 13 and 18 detection). In one analysis, the z score approach was used to determine the trisomy status by comparing the test samples with the control samples (euploid samples). Therefore, this statistical method uses several control samples to be sequenced. In this study, four euploid samples were sequenced in each sequencing run and a total of 103 euploid cases were sequenced as the control samples (13 of them have been sequenced twice in different sequencing runs). This approach markedly increased the sequencing cost for trisomy 13 and 18 diagnosis.

However, except for the trisomic chromosome, the remaining chromosomes are normal in the genome of a trisomy fetus. Therefore, instead of comparing the test sample with normal samples, one could compare the test chromosome with the normal chromosomes within one sample to determine the trisomy status of the test sample.

Comparing Chr13 or Chr18 with Other Chromosomes within the Sample

Instead of comparing the test sample with the control samples by the z score approach, the trisomy status will be determined by comparing the test chromosome, e.g. chr13 or chr18, with the other chromosome within the sample. To achieve this, the sequenced reads were analyzed as previously described. The genome was divided into 500 kb consecutive bins. The GC correction with LOESS regression was used to reduce the GC bias in the read counts. After GC correction, the GC-corrected read counts from chr13 or chr18 were compared with other chromosomes by Wilcoxon Rank Sum test. The chromosome 21, X and Y were excluded for comparison. The p value cutoff 0.05 was used to determine the trisomy status. Since no control samples were needed in this analysis, all the control samples in the previous analysis were used as the test samples.

Figure 8A:
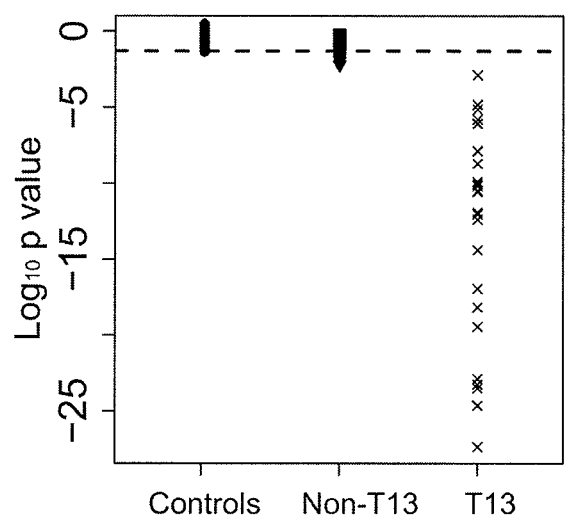
FIGS. 8A and 8B. Trisomy 13 and 18 detection by comparing chr13 or chr18 with other chromosomes. The whole genome was divided into 500 kb bins and the number of read counts for each bin was calculated. The read counts from chr13 or chr18 were compared with those from other chromosomes by the Wilcoxon Rank Sum test. The p value was plotted for (A) trisomy 13 and (B) trisomy 18 detection. Since no control samples were needed, those control samples in the previous analysis were test samples in this analysis. Dashed line indicated the diagnostic cutoff with p value of 0.05. T13, trisomy 13. T18, trisomy 18.
Figure 8B:
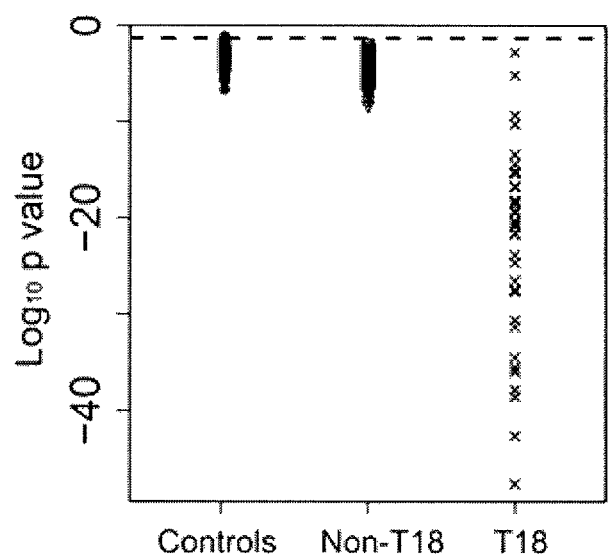

Instead of comparing chr13 or chr18 among samples by the z score approach, the trisomy 13 and 18 status was determined by comparing chr13 or chr18 with other chromosomes within the sample. After the GC correction, the p value for each sample by the Wilcoxon Rank Sum test was calculated (FIGS. 8A and 8B). By using the p value cutoff 0.05, out 25 trisomy 13 cases and 246 out of 264 non-trisomy 13 cases were correctly identified, corresponding to a sensitivity and specificity 100% and 93.2%, respectively. For trisomy 18, 37 out of 37 trisomy 18 cases but no non-trisomy 18 cases were identified correctly, corresponding to a sensitivity and specificity 100% and 0%, respectively.

In FIGS. 8A and 8B, it is showed that the trisomy cases have smaller p values than the non-trisomy cases. These results indicated that it was feasible to compare the chromosomes within the sample to determine the trisomy status. However, by using a fix cutoff (p value=0.05), the performances for trisomy 13 and 18 detection were markedly different.

Figure 8C:
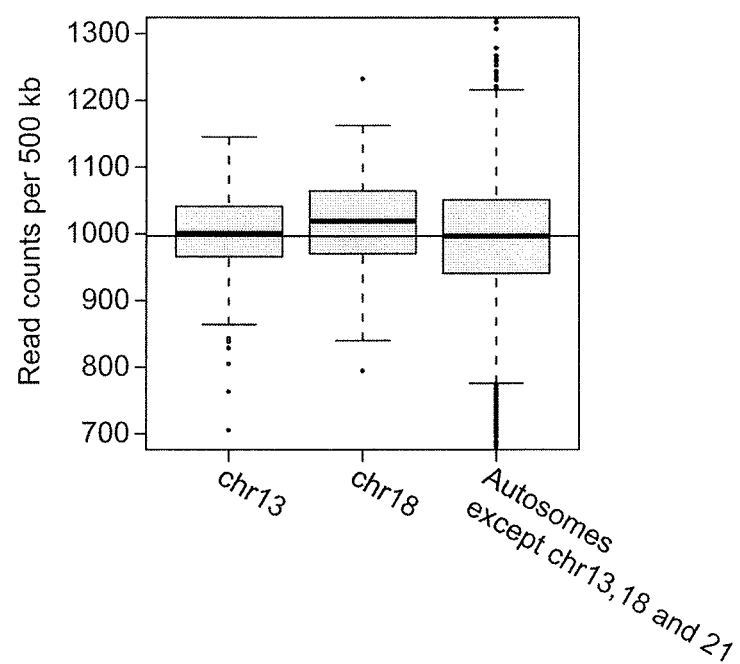
FIG. 8C. The distribution of read counts per 500 kb for chr13, 18 and other autosomes except chr21 after GC correction. The boxplot of read counts per 500 kb bin from a euploid sample. The median read counts per bin from chr13 and chr18 is higher than those from other autosomes (except chr21). This trend was also observed in other euploid samples. Dashed line indicated the median read counts per bin of the other autosomes (except chr21).
Figure 9A:
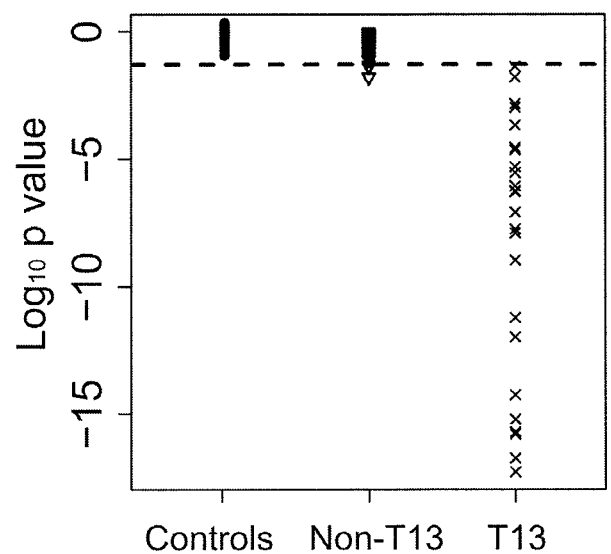
FIGS. 9A and 9B. Trisomy 13 and 18 detection by comparing chr13 or chr18 with artificial chromosomes. Two artificial chromosomes with the similar GC contents and mappability to chr13 and chr18 were constructed, respectively. The read counts from chr13 or chr18 were compared with those from artificial chromosomes by the Wilcoxon Rank Sum test. The p value was plotted for (A) trisomy 13 and (B) trisomy 18 detection. Since no control samples were needed, those control samples in the previous analysis were test samples in this analysis. Dashed line indicated the diagnostic cutoff with p value of 0.05. T13, trisomy 13. T18, trisomy 18.
Figure 9B:
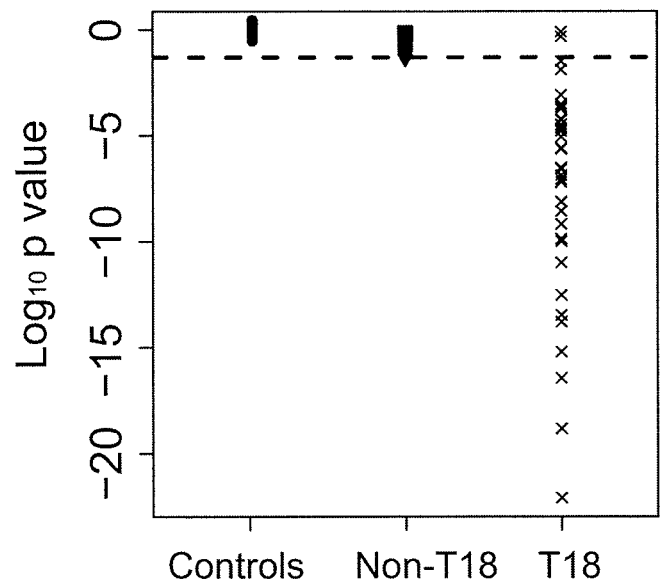

To examine the reason, the read counts distribution for chr13, 18 and other autosomes (except chr21) from a euploid sample was plotted after GC correction (FIG. 8C). It has been observed that the median read counts per 500 kb bin of chr13 and chr18 was higher than those of autosomes (except chr21) in the euploid sample. Therefore, if one compared chr13 and 18 with the autosomes (except chr21) to determine the trisomy 13 and 18 status, this would cause a relatively high false positive rate.

Comparing Chr13 or Chr18 with the Artificial Chromosomes

Two artificial chromosomes were constructed for comparison reference. One was for chr13, termed artificial chr13, the other was for chr18, termed artificial chr18. The artificial chromosome was constructed as following. The whole genome was divided into 500 kb bins. For each of the bin in chr13, three bins from other chromosomes (autosomes except chr13, chr18 and chr21) were chosen. These three bins typically have the same GC contents and mappability as the corresponding bin in chr13. Therefore each bin in chr13 was corresponded to three bins in the artificial chr13. The artificial chr13 was constructed by combined all the bins that have same GC contents and mappability as the bins in chr13. The artificial chr18 was constructed in the same way. The GC correction with LOESS regression was used to reduce the GC bias in the read counts. After GC correction, the GC-corrected read counts from chr13 or chr18 were compared with that from the artificial chr13 and ch18 by Wilcoxon Rank Sum test. The p value cutoff 0.05 was used to determine the trisomy status. Since no control samples were needed in this analysis, all the control samples in the previous analysis were used as the test samples.

Theoretically, if there is no bias in the NGS data, the read counts distribution should be similar across different chromosomes in the euploid sample. However, it has been observed that this is not the case. This is probably due to two factors result in the different read counts different among chromosomes. One major factor is the mappability of different chromosomes. Since only the uniquely aligned reads were retained for analysis, regions with different mappability might have different uniquely aligned reads. A week correlation between the read counts and the mappability was observed (Spearman's rank correlation coefficient=0.257). The other factor is the remaining GC bias in read counts after GC correction. It would be expected that using the "chromosomes" with similar GC and mappability as the comparison references to chr13 and chr18 would counteract this affect.

In order to address this problem, two artificial chromosomes that have the similar GC contents and mappability to chr13 and chr18 had been constructed, called artificial chr13 and artificial chr18, respectively. By using the artificial chromosomes as the comparison references and a fixed p value cutoff of 0.05, 25 out 25 trisomy 13 cases and 260 out of 264 non-trisomy 13 cases were correctly identified, corresponding to a sensitivity and specificity 100% and 98.5%, respectively. Since no control samples were needed in this analysis, the previous euploid control samples used in the z score approach were also considered as the test samples. All the euploid "control" samples were correctly identified, resulting in a final specificity of 98.9%. For trisomy 18, 35 out of 37 trisomy 18 cases and 251 out of 252 non-trisomy 18 cases were identified correctly, corresponding to a sensitivity and specificity 94.6% and 99.6%, respectively. All the euploid "control" samples were correctly identified, resulting in a final specificity of 99.7%.

In this section, a third step of the bioinformatics analysis pipeline, the statistics for trisomy (e.g. 13 and 18) detection, had been improved. A new statistics that compared chr13 or chr18 with the artificial chr13 or chr18 had been developed. In this new trisomy detection method, no controls samples were needed. Therefore, the sequencing cost for trisomy 13 and 18 detection could be reduced. Compared with the z score approach, the performance of the trisomy 13 and 18 detection had further improved by new statistics.

After the GC correction, the bias of read counts for different chromosomes still existed. Compared with the chr21, the chr18 and chr13 were over represented even in a euploid sample by calculating the GC-corrected read counts. These results indicated that the bias still existed and thus the read counts from different chromosomes could not be compared directly. The artificial chromosomes were constructed to correct the bias and most importantly, no control samples were needed.

After the improvement in the three steps of the bioinformatics analysis pipeline, the performance of the trisomy 13 and 18 detection had been greatly improved and was also compatible to that for trisomy 21 detection. Most importantly, all the improvement were only made in the bioinformatics aspects. Thus, those modifications to the analysis pipeline would not increase the cost of the trisomy 13 and 18 detection by NGS.

V. Region-Selecting Method

FIG. 1 is a flow chart showing a method of reducing GC bias by aligning sequences obtained from a biological sample (e.g., maternal plasma) with an artificial chromosome. The method can be used to determine an amplification or deletion of a genomic region. The sample may be a mixture that includes cell-free DNA from a fetus and from a female pregnant with the fetus. In another example, the sample may be a mixture that includes cell-free DNA from a tumor and from a patient.

In step 11, GC content is determined in a chromosomal region of interest (first chromosomal region). The GC content can be defined in a variety of ways, e.g., as described herein. The GC content can be determined from a reference genome.

In step 12, an artificial reference chromosome can be identified by identifying disjointed regions having about the same GC content as the chromosomal region of interest.

The disjointed regions can collectively have the same GC content or each can individually have about the same GC content. Thus, a region can be selected if it brings an average GC content for all of the regions to be about the same GC content.

The disjoint regions can be selected from various chromosomes or from just one chromosome. The disjoint regions and the chromosomal region of interest may even be selected from a same chromosome, if the one section for the reference is known to have a normal copy number (e.g., 2 for autosomes), i.e., no amplification or deletion.

In step 13, sequence tags obtained from a sequencing of a biological sample (e.g., maternal plasma) with the artificial reference chromosome and with the chromosomal region of interest. The sequence tags may be received at a computer system.

In step 14, a first amount of sequence tags that align with the first chromosomal region are determined. The first amount can be a number of tags, a length of tags, or a length of DNA fragments (e.g., if paired-end sequencing is performed).

In step 15, a second (reference) the amount of sequence tags that align with the artificial reference chromosome can be determined. In one embodiment, the aligning can be done only to the regions corresponding to the first chromosomal region and the artificial reference chromosome.

In step 16, a parameter is determined from the first amount and the reference amount. As examples, the parameter can be a ratio or a difference. The parameter may be determined from a function of the ratio and/or difference.

In step 17, the parameter is compared to a cutoff value, thereby characterizing the chromosomal region of interest. The cutoff can signify whether the parameter is statistically different than a reference value, where the reference value can be determined from a healthy person or determined theoretically. The cutoff can depend on the lengths of the first chromosomal region and the artificial reference chromosome. For example, if the parameter is a ratio of the amounts, then the cutoff and a reference value would about for the difference in lengths. For instance if the first chromosomal region is twice as long as the artificial reference chromosome, then the reference value might be 0.5 and a cutoff might a certain amount above or below 0.5 (e.g., as determined by a standard deviation from the reference value). If the reverse were true, then the reference value might be 2.

In some embodiments, the first chromosomal region may be divided up into disjoint subregions. These subregions may be selected in a same manner as the regions of the artificial reference chromosome. The subregions can be selected so that the first chromosomal region and the artificial reference chromosome have about the same GC content. The range of the GC contents being the same can be specified by a user or values can be used as a default. For example, the GC contents can be specific to be within a few percent of each other. Other regions can be added until the GC contents are within an acceptable range.

The various regions and subregions can be the same length or be of different lengths. The average GC content for a collection of disjoint regions can be determined and account for the different lengths.

VI. EXAMPLE

Patau syndrome, also known as trisomy 13(T13), is a syndrome in which a patient has an additional chromosome 13 due to a non-disjunction of chromosomes during meiosis[1]. Therefore, chromosome 13 is also an important target for noninvasive prenatal diagnosis of fetal chromosomal abnormalities.

Figure 10A:
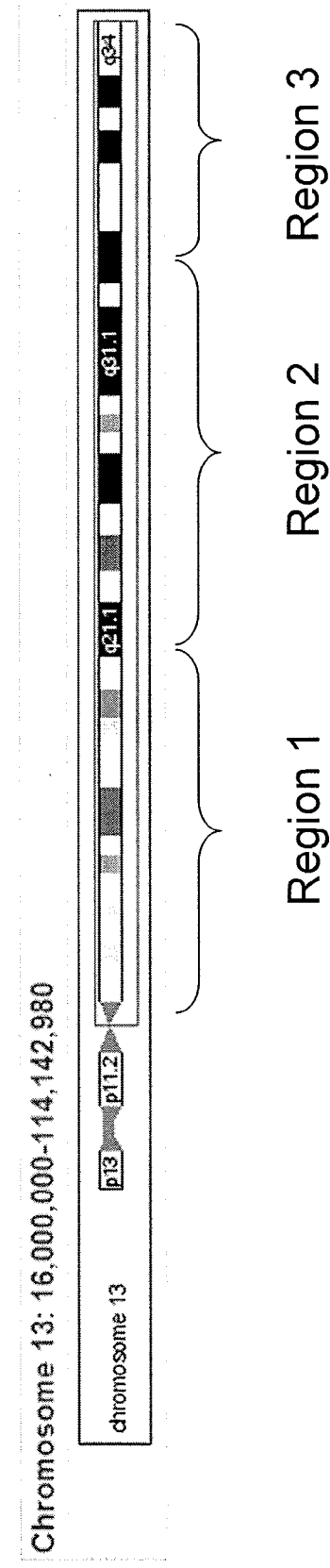

The DNA sequence analysis of human chromosome 13 demonstrates that it contains a central 'gene desert' region of 37.8 Mb, where the gene density drops to only 3.1 genes per Mb and the overall GC content drops to 33%[4]. This is named as region 2 in FIG. 10A. In contrast, the most gene-rich regions are at either end of the long arm of this chromosome, namely regions 1 and 3 as shown in FIG. 10A. Both regions 1 and 3 have a GC content of 39%.

Accordingly, a region-selecting method was employed to minimize the effects caused by variations in the GC content on the reproducibility of the chromosomal genomic representations obtained by sequencing. The long arm of chromosome 13 was divided into three regions: Region1 (16-52.9 Mb), Region2 (52.9-90.7 Mb) and Region3 (90.7-114.1 Mb). Discarded were the unique reads that mapped perfectly to the reference human genome, termed U0-1-0-0 sequence reads, mapped to Region2 and reserved the U0-1-0-0 sequence reads of Region 1 and Region3. The new percentage of genomic representation of chromosome 13 was calculated by dividing the remaining U0-1-0-0 counts from chromosome 13 by the updated sum of U0-1-0-0 sequence reads from the whole genome which was determined by subtracting the U0-1-0-0 counts of Region2 from the previous total number of U0-1-0-0 sequence reads obtained from the sequencing run. A schematic illustration of the data analysis steps are shown in FIG. 10B. The mean and SD of the percentage of chromosome 13 were recalculated using the same euploid samples, and subsequently the coefficient of variation (CV=SD/mean×100%) was calculated. With these new reference values, the z-score of chromosome 13 was obtained for each case.

Figure 10C:
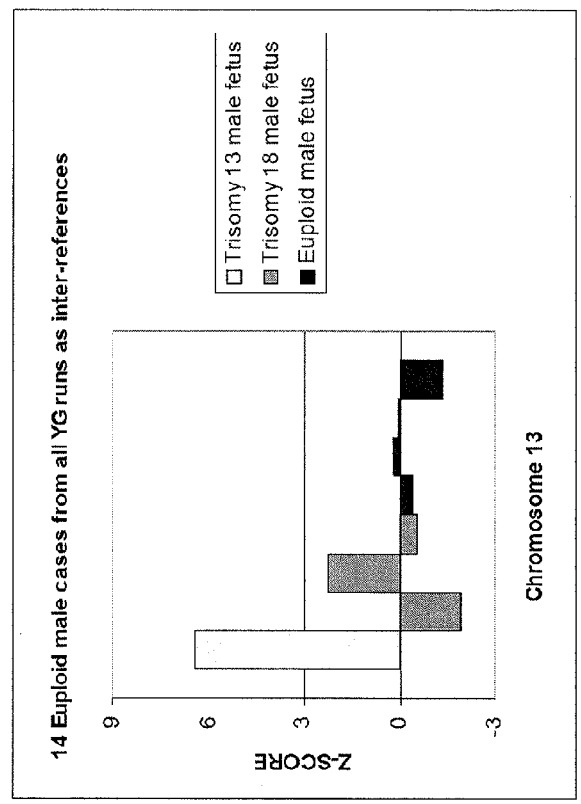
Figure 10C:
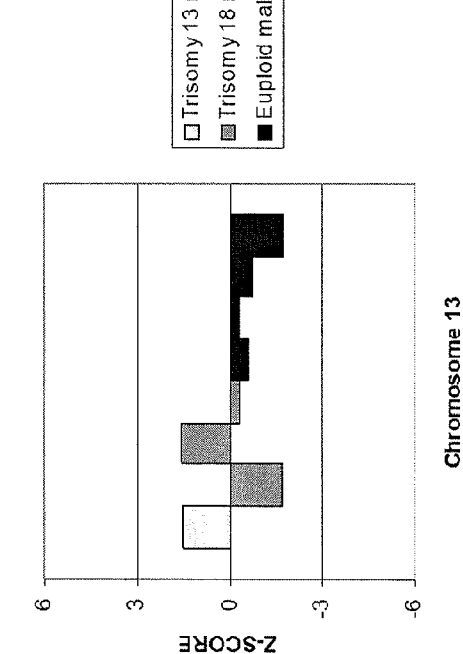
Figure 11:
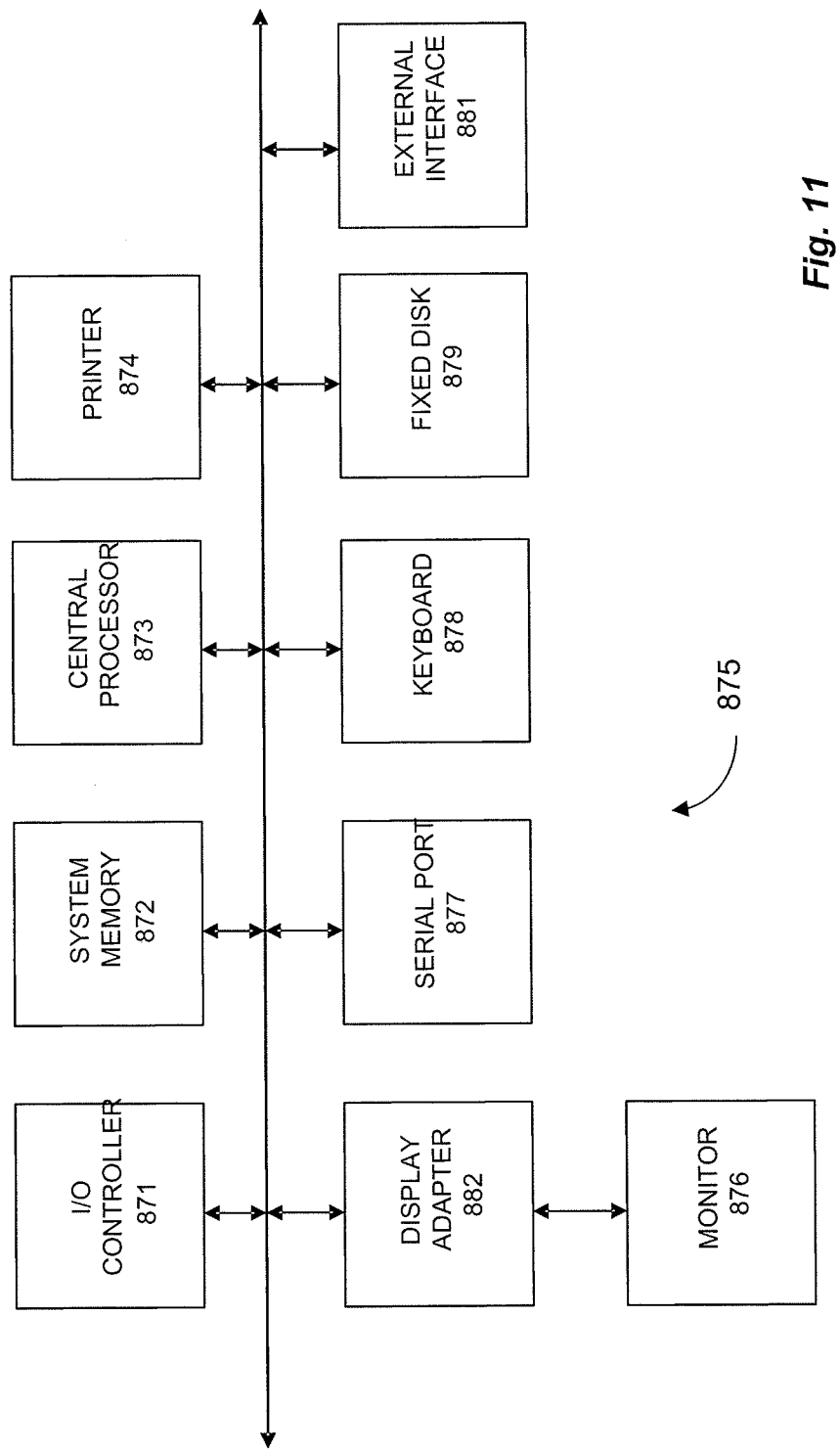
FIG. 11 is a block diagram of an example computer system 800 usable with system and methods according to embodiments of the present invention.

Applying this region-selecting method to a previous dataset, a decrease in the CV of chromosome 13 could be observed from 3.41% to 0.97%. Also the z-score of a T13 case increased from 1.22 to 5.76, which correctly identified the T13 fetus with z-score >3 being cutoff (FIG. 10C).

Therefore, this region-selecting method can increase the sensitivity of aneuploidy detection and enhance the precision for noninvasive prenatal diagnosis of T13 when using the massively parallel sequencing approach.

VII. Computer System

Any of the computer systems mentioned herein may utilize any suitable number of subsystems. Examples of such subsystems are shown in FIG. 8 in computer apparatus 800. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 8 are interconnected via a system bus 875. Additional subsystems such as a printer 874, keyboard 878, fixed disk 879, monitor 876, which is coupled to display adapter 882, and others are shown. Peripherals and input/output (I/O) devices, which couple to I/O controller 871, can be connected to the computer system by any number of means known in the art, such as serial port 877. For example, serial port 877 or external interface 881 (e.g. Ethernet, Wi-Fi, etc.) can be used to connect computer system 800 to a wide area network such as the Internet, a mouse input device, or a scanner. The interconnection via system bus 875 allows the central processor 873 to communicate with each subsystem and to control the execution of instructions from system memory 872 or the fixed disk 879, as well as the exchange of information between subsystems. The system memory 872 and/or the fixed disk 879 may embody a computer readable medium. Any of the values mentioned herein can be output from one component to another component and can be output to the user.

A computer system can include a plurality of the same components or subsystems, e.g., connected together by external interface 881 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned above are hereby incorporated herein by reference in their entireties for all purposes.

What is claimed is:

1. A method of characterizing a test genome or portion thereof, the method comprising:
   identifying a first chromosomal region having a first GC content in a reference genome;
   assembling an artificial reference chromosome including a plurality of disjoint regions of the reference genome, the plurality of disjoint regions being at least 50 kb in length, the artificial reference chromosome having a second GC content that is about the first GC content;
   aligning, by a computer system, each of a plurality of sequence tags with the first chromosomal region and with the artificial reference chromosome, wherein the sequence tags have been obtained by sequencing nucleic acids in a biological sample comprising cell-free nucleic acids from a first tissue and a second tissue;
   determining, by a computer system, a first amount of sequence tags that align with the first chromosomal region;
   determining, by a computer system, a reference amount of sequence tags that align with the artificial reference chromosome;
   determining a parameter from the first amount and the reference amount, the parameter including a ratio of the first amount and the reference amount; and
   comparing the parameter to a cutoff value, thereby determining a classification of an amplification or deletion in the first chromosomal region of the first tissue.

2. The method of claim 1, wherein the first tissue is from a fetus and the second tissue is from a female pregnant with the fetus.

3. The method of claim 1, wherein the first tissue is from a tumor and the second tissue is from healthy cells of a patient having the tumor.

4. The method of claim 1, wherein the first chromosomal region includes a plurality of disjoint subregions.

5. The method of claim 1, wherein the plurality of disjoint regions are from the same chromosome.

6. The method of claim 1, wherein the plurality of disjoint regions are from different chromosomes.

7. The method of claim 1, wherein all the plurality of disjoint regions together have the first GC content within a specified percentage.

8. The method of claim 7, wherein each of the disjoint regions separately has the first GC content within the specified percentage.

9. The method of claim 1, wherein the biological sample is maternal plasma.

10. The method of claim 1, wherein the genome is human, wherein the first chromosomal region is part of a chromosome selected from chromosome 13, chromosome 18, or chromosome 21, and wherein the classification is trisomy of said chromosome.

11. The method of claim 1, wherein the disjoint regions were obtained by sequencing nucleic acids in the sample.

12. A computer program product comprising a non-transitory computer readable medium storing a plurality of instructions for controlling a processor to perform an operation, the instructions comprising:
   identifying a first chromosomal region having a first GC content;
   assembling an artificial reference chromosome including a plurality of disjoint regions of the reference genome, the plurality of disjoint regions being at least 50 kb in length, the artificial reference chromosome having a second GC content that is about the first GC content;
   aligning each of a plurality of sequence tags with the first chromosomal region and with the artificial reference chromosome, wherein the sequence tags have been obtained by sequencing nucleic acids in a biological sample comprising cell-free nucleic acids from a first tissue and a second tissue;
   determining a first amount of sequence tags that align with the first chromosomal region;
   determining a reference amount of sequence tags that align with the artificial reference chromosome;
   determining a parameter from the first amount and the reference amount, the parameter including a ratio of the first amount and the reference amount; and
   comparing the parameter to a cutoff value, thereby determining a classification of an amplification or deletion in the first chromosomal region of the first tissue.

13. A system comprising one or more processors configured for characterizing a genome or portion thereof by a process that comprises:
  identifying a first chromosomal region that has a first GC content;
  assembling an artificial reference chromosome including a plurality of disjoint regions of the reference genome, the plurality of disjoint regions being at least 50 kb in length, the artificial reference chromosome having a second GC content that is about the first GC content;
  aligning each of a plurality of sequence tags determined for a biological sample with the first chromosomal region and with the artificial reference chromosome;
  determining a first amount of sequence tags that align with the first chromosomal region;
  determining a reference amount of sequence tags that align with the artificial reference chromosome;
  determining a parameter from the first amount and the reference amount, the parameter including a ratio of the first amount and the reference amount; and
  comparing the parameter to a cutoff value, thereby determining a classification of an amplification or deletion in the biological sample.

14. The method of claim 1, further comprising sequencing at least part of the cell-free nucleic acids of the first tissue and at least part of the cell-free nucleic acids of the second tissue before the aligning.

15. The method of claim 14, wherein the biological sample is plasma.

16. The method of claim 1, wherein the parameter is a probability value that the first amount and the reference amount are statistically different.

17. The method of claim 16, wherein the cutoff value is 0.05.

18. The method of claim 1, wherein identifying the first chromosomal region comprises selecting gene-rich regions.

19. The method of claim 1, wherein identifying the first chromosomal region comprises selecting regions at either end of the long arm of chromosome 13 and excluding regions in between.

20. The computer program product of claim 12, wherein the parameter is a probability value that the first amount and the reference amount are statistically different.

21. The computer program product of claim 20, wherein the cutoff value is 0.05.

22. The computer program product of claim 12, wherein identifying the first chromosomal region comprises selecting gene-rich regions.

23. The computer program product of claim 12, wherein identifying the first chromosomal region comprises selecting regions at either end of the long arm of chromosome 13 and excluding regions in between.

24. The computer program product of claim 12, wherein the instructions further comprise correcting GC bias in the first amount and the reference amount by regression analysis.

25. The method of claim 1, wherein the assembling of the artificial chromosome comprises assembling disjoint regions having both about the same GC content and about the same mappability as the first chromosomal region.

26. The method of claim 25, wherein the first chromosomal region is chromosome 13, and the artificial reference chromosome has about the same GC content and about the same mappability as chromosome 13.

27. The method of claim 25, wherein the first chromosomal region is chromosome 18, and the artificial reference chromosome has about the same GC content and about the same mappability as chromosome 18.

28. The computer program product of claim 12, wherein the instructions for assembling of the artificial chromosome comprise instructions for assembling disjoint regions having both about the same GC content and about the same mappability as the first chromosomal region.

29. The method of claim 1, further comprising:
  displaying, by the computer system, the classification of the amplification or deletion in the first chromosomal region of the first tissue.

30. The method of claim 1, wherein the second GC content that is within at least 2.7% of the first GC content.

* * * * *